(12) United States Patent
Kentsis et al.

(10) Patent No.: US 11,208,446 B2
(45) Date of Patent: Dec. 28, 2021

(54) AGENTS AND METHODS FOR TREATING CBP-DEPENDENT CANCERS

(71) Applicant: Memorial Sloan Kettering Cancer Center, New York, NY (US)

(72) Inventors: Alex Kentsis, New York, NY (US); Kavitha Ramaswamy, New York, NY (US); Lauren Marek, New York, NY (US)

(73) Assignee: MEMORIAL SLOAN KETTERING CANCER CENIER, New York, NY (US)

( * ) Notice: Subject to any disclaimer, the term of this patent is extended or adjusted under 35 U.S.C. 154(b) by 76 days.

(21) Appl. No.: 16/346,834

(22) PCT Filed: Nov. 1, 2017

(86) PCT No.: PCT/US2017/059579
§ 371 (c)(1),
(2) Date: May 1, 2019

(87) PCT Pub. No.: WO2018/085436
PCT Pub. Date: May 11, 2018

(65) Prior Publication Data
US 2019/0276509 A1    Sep. 12, 2019

Related U.S. Application Data

(60) Provisional application No. 62/415,800, filed on Nov. 1, 2016.

(51) Int. Cl.
*C07K 14/47* (2006.01)
*A61P 35/02* (2006.01)
*A61K 38/00* (2006.01)

(52) U.S. Cl.
CPC .......... *C07K 14/4705* (2013.01); *A61P 35/02* (2018.01); *A61K 38/00* (2013.01); *C07K 2319/10* (2013.01)

(58) Field of Classification Search
CPC ...................... C07K 14/4705; C07K 2319/10; A61K 38/00; A61P 35/02
See application file for complete search history.

(56) References Cited

U.S. PATENT DOCUMENTS

| | | |
|---|---|---|
| 2002/0106767 A1 | 8/2002 | Rana et al. |
| 2008/0090770 A1 | 4/2008 | Belmares et al. |
| 2009/0062178 A1 | 3/2009 | Harrison |
| 2012/0270800 A1 | 10/2012 | Verdine et al. |
| 2012/0302503 A1 | 11/2012 | Hurtt |

FOREIGN PATENT DOCUMENTS

| | | | | |
|---|---|---|---|---|
| EP | 1884521 A1 * | 2/2008 | ............... | C07K 7/08 |
| WO | WO 01/38547 A2 | 5/2001 | | |

OTHER PUBLICATIONS

International Search Report for PCT application No. PCT/US2017/059579 dated Mar. 1, 2018.

* cited by examiner

*Primary Examiner* — Li N Komatsu
(74) *Attorney, Agent, or Firm* — Mark S. Cohen; Pearl Cohen Zedek Latzer Baratz LLP

(57) ABSTRACT

Single chain peptides comprising either a cell penetrating HIV-TAT peptide sequence and a MYB:CBP complex interfering peptide sequence from MYB, or comprising a cell penetrating HIV-TAT peptide sequence, a CBP binding peptide sequence from CREB and a MYB:CBP complex interfering peptide sequence from MYB, are provided for use in preventing MYB:CBP complex formation and downstream events leading to cancer, in particular a leukemia. Both L-amino acid single chain peptides and retro-inverso single chain peptides are provided.

9 Claims, 9 Drawing Sheets

Specification includes a Sequence Listing.

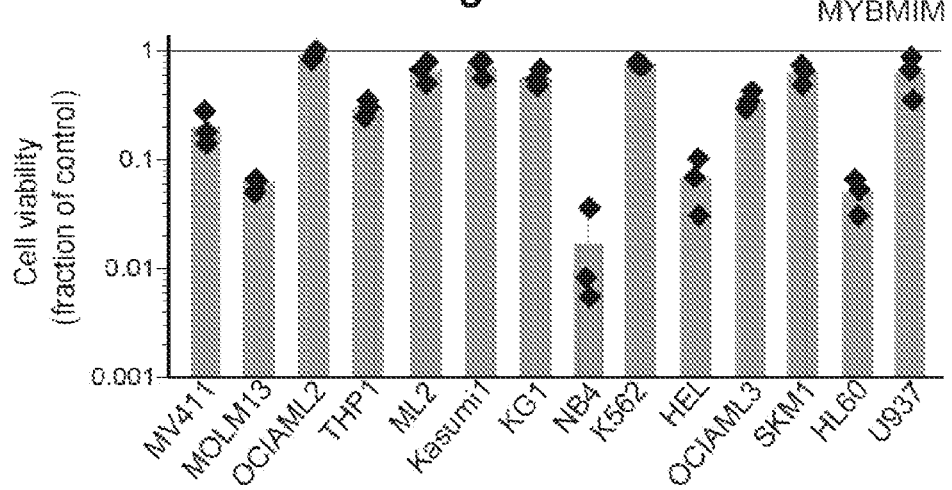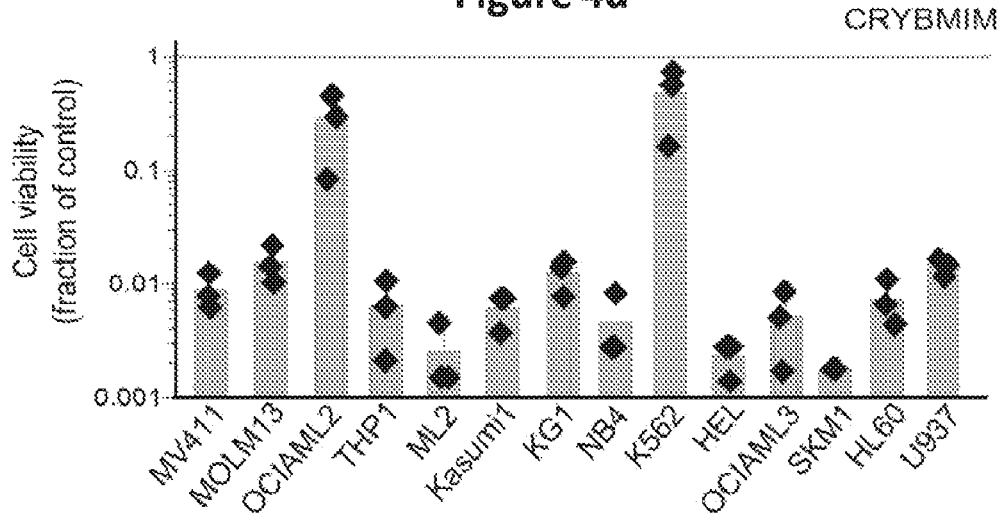

AGENTS AND METHODS FOR TREATING CBP-DEPENDENT CANCERS

CROSS-REFERENCE TO RELATED APPLICATION

This application is a National Phase Application of PCT International Application No. PCT/US2017/059579, international filing date Nov. 1, 2017, claiming the benefit of U.S. Provisional Application No. 62/415,800, filed Nov. 1, 2016, which are hereby incorporated by reference.

BACKGROUND OF THE INVENTION

In spite of substantial efforts, therapy of pediatric and adult acute myeloid leukemia (AML) has not had significant improvements over the last 30 years with outcomes particularly poor for patients with high-risk molecular features and those whose disease is resistant to intensive combination chemotherapy. Both myeloid and lymphoblastic leukemias depend on the aberrant activity of key molecular regulators of gene transcription. Central to this molecular mechanism is the transcription factor MYB, which is a sequence-specific DNA binding protein that trans-activates expression of genes important for leukemia cell growth and survival. Among MYB's various binding partners, CBP, or CREB-binding protein, is an important co-activator that interacts with the transactivation domain of MYB and exerts histone acetyltransferase activity fundamental in downstream gene regulation.

MYB has been implicated as a human leukemia oncogene, among other cancers, with abnormalities in MYB seen in various leukemias, both acute and chronic. In addition to point mutations and truncation mutations in MYB, there is evidence of overexpression of MYB in ALL. MYB has been repeatedly identified as a molecular requirement for the initiation and maintenance of a wide variety of AML subtypes in xenografts and genetically-engineered mouse leukemia models. MYB particularly plays an important role in the leukemogenic maintenance of MLL-rearranged leukemias, as shown by the marked survival in vivo of mice with an inducible MYB shRNA knock down system. In an engineered mouse model that associates a requirement of the MYB:CBP complex in the initiation of AML, Myb mutant cells harboring a E308G mutation in the MYB:CBP interface were unable to transform to AML with either the AML1-ETO or MLL-AF9 oncogenes.

Translation of this knowledge into therapies to block leukemogenic MYB activity is hindered by the pharmacologic challenges of targeting transcription factors and protein-protein interactions. The necessary intranuclear physical interactions between transcription factors and their co-activators provides a site-specific mark for potential drug targets.

It is towards new means of blocking leukemogenic MYB activity as well as for the treatment of various cancers that the present invention is directed.

BRIEF DESCRIPTION OF THE INVENTION

In one embodiment, the invention is directed to a single chain peptide comprising a cell penetrating peptide sequence from HIV-TAT and a CBP binding peptide sequence from MYB. In one embodiment the single chain peptide is comprised of L-amino acids. In one embodiment the sequence from HIV-TAT is at the N-terminal part of the single chain peptide, and the sequence from MYB is at the C-terminal part. In one embodiment, the sequence in the single chain peptide from HIV-TAT is L-amino acid sequence YGRKKRRQRRR (SEQ ID NO:16). In one embodiment, the sequence in the single chain peptide from MYB is L-amino acid sequence KRIKELELLLMSTENELK (SEQ ID NO:18). In one embodiment, the cell penetrating peptide sequence from HIV-TAT and the CBP binding peptide sequence from MYB are joined by a linker. In one embodiment, the linker comprises one or more amino acids. In one embodiment, the linker is GG.

In one embodiment, the single chain peptide has the L-amino acid sequence YGRKKRRQRRRGGKRIKELELLLMSTENELK (SEQ ID NO:2).

In one embodiment, the cell penetrating peptide sequence from HIV-TAT and the CBP binding peptide sequence from MYB are comprised of D-amino acids, and the order of amino acids is inverted from that in the L-amino acid sequence (i.e., a retro-inverso sequence). In one embodiment, the retro-inverso sequence from MYB is at the N-terminal part of the single chain peptide, and the retro-inverso sequence from HIV-TAT is at the C-terminal part. In one embodiment, the cell penetrating peptide sequence from HIV-TAT is the D-amino acid sequence RRRQRRKKRGY (SEQ ID NO:17). In one embodiment, the CBP binding peptide sequence from MYB is the D-amino acid sequence KLENETSMLLLELEKIRK (SEQ ID NO:19). In one embodiment, the cell penetrating peptide sequence from HIV-TAT and the CBP binding peptide sequence from MYB are joined by a linker. In one embodiment the linker comprises one or more amino acids. In one embodiment, the linker is GG.

In one embodiment, the single chain peptide has the D-amino acid sequence KLENETSMLLLELEKIRKGGRRRQRRKKRGY (SEQ ID NO:1).

In one embodiment, each of the cell penetrating peptide sequence from HIV-TAT, the CBP binding peptide sequence from MYB peptide, or both, in the single chain peptide comprises one or more amino acid additions, deletions or substitutions, or the N-terminus is acetylated, the C-terminus is amidated, or any combination thereof. In one embodiment, each of the cell penetrating peptide sequence from HIV-TAT, the CBP binding peptide sequence from MYB, or both, in the single chain peptide independently has at least 98%, at least 95%, at least 90%, at least 85%, at least 80% or at least 75% sequence identity with the respective HIV-TAT and MYB sequences within SEQ ID NOS: 1 and 2.

In one embodiment, the single chain peptide has the L-amino acid sequence [Ac]-YGRKKRRQRRRGGKRIKELELLLMSTENELK-[NH2] (SEQ ID NO:2) and in one embodiment, the single chain peptide has the D-amino acid sequence [Ac]-KLENETSMLLLELEKIRKGGRRRQRRKKRGY-[NH2] (SEQ ID NO:1). [Ac] represents an acetyl group at the N terminus, and [NH2] represents an amide at the C terminus.

In one embodiment, one of the sequence from HIV-TAT or the sequence from MYB comprises L-amino acids, and the other sequence comprises D-amino acids in the reverse order (i.e., retro-inverso).

In one embodiment, the invention is directed to a single chain peptide comprising a cell penetrating peptide sequence from HIV-TAT, a CBP binding peptide sequence from CREB, and a CBP binding peptide sequence from MYB. In one embodiment the single chain peptide is comprised of L-amino acids. In one embodiment the sequence from HIV-TAT is at the N-terminal part of the single chain peptide, the sequence from MYB is at the C-terminal part, and the sequence from CREB is between them. In one embodiment, the sequence in the single chain peptide from HIV-TAT is the L-amino acid sequence YGRKKRRQRRR (SEQ ID NO:16). In one embodiment, the sequence of the CBP binding peptide sequence from CREB is the L-amino acid sequence RREILSRRPpSYRK (SEQ ID NO:20), and the sequence in the single chain peptide from MYB is L-amino acid sequence LELLLMSTENELK (SEQ ID NO:21). In one embodiment, the cell penetrating peptide sequence from HIV-TAT and the CBP binding peptide sequence from MYB are joined by a linker. In one embodiment, the linker is GG. The CBP binding peptide sequence from MYB and the CBP binding peptide sequence from CREB may also be joined by a linker. In one embodiment, the order of these sequences in the L-amino acid, single-chain peptide is, from the N-to-C terminus, is the sequence from HIV-TAT, the sequence from CREB, sequence from MYB. In another embodiment, the order is the L-amino acids is the sequence from HIV-TAT, the sequence from MYB and the sequence from CREB.

In one embodiment, the single chain peptide has the L-amino acid sequence YGRKKRRQRRRGGR-REILSRRPpSYRKLELLLMSTENELK (SEQ ID NO:22).

In one embodiment, the cell penetrating peptide sequence from HIV-TAT, the CBP binding peptide sequence from CREB, and the CBP binding peptide sequence from MYB are composed of D-amino acids, and the order of amino acids is reversed from that of the L-amino acid sequence (i.e., a retro-inverso peptide). In one embodiment, the sequence from HIV-TAT is the D-amino acid sequence RRRQRRKKRGY (SEQ ID NO:17). In one embodiment the CBP binding peptide sequence from CREB is the D-amino acid sequence KRYpSPRRSLIERR (SEQ ID NO:23). In one embodiment, the CBP binding peptide sequence from MYB is the D-amino acid sequence KLE-NETSMLLLEL (SEQ ID NO:24). In one embodiment, the order of these sequences in the single-chain peptide is, from the N-to-C terminus, is the retro-inverso sequence from MYB, the retro-inverso sequence from CREB, and the retro-inverso sequence from HIV-TAT. In another embodiment, the order from N-to-C is the retro-inverso sequences is the sequence from CREB, the sequence from MYB, and the sequence from HIV-TAT.

In one embodiment, the single chain peptide has the D-amino acid sequence KLENETSMLL-LELKRYpSPRRSLIERRGGRRRQRRKKRGY (SEQ ID NO:25).

In one embodiment, one of the sequence from HIV-TAT, the sequence from MYB, and the sequence from CREB is comprised of L-amino acids, and the other sequences comprise retro-inverso sequences. In another embodiment, two among the sequence from HIV-TAT, the sequence from MYB, and the sequence from CREB are comprised of L-amino acids, and the other sequence is retro-inverso.

In one embodiment, each of the cell penetrating peptide sequence from HIV-TAT, the CBP binding peptide sequence from CREB, and the CBP binding peptide sequence from MYB peptide, or two or three of these sequences within the single chain peptide, comprises one or more amino acid additions, deletions or substitutions, or the N-terminus is acetylated, the C-terminus is amidated, or any combination thereof. In one embodiment, each of the cell penetrating peptide sequence from HIV-TAT, the CBP binding peptide sequence from CREB, the CBP binding peptide sequence from MYB, or two or three of these sequences within the single chain peptide, independently has at least 98%, at least 95%, at least 90%, at least 85%, at least 80% or at least 75% sequence identity with the respective sequence of the HIV-TAT, CREB, and MYB sequences within SEQ ID NOS: 16, 20 and 18, respectively. Furthermore, the single chain peptide of this embodiment may comprise longer or shorter fragments of the three respective components, as further described below. The embodiments apply to either the L-amino acid or D-amino acid/reversed sequences of the invention.

In one embodiment, the single chain peptide has the L-amino acid sequence [Ac]-YGRKKRRQRRRGGR-REILSRRPpSYRKLELLLMSTENELK-[NH2] (SEQ ID NO:26) and in one embodiment, the single chain peptide has the D-amino acid sequence [Ac]-KLENETSMLL-LELKRYpSPRRSLIERRGGRRRQRRKKRGY-[NH2] (SEQ ID NO:27). In different embodiments, the N-terminus may be acetylated, the C-terminus amidated, or the combination of both. [Ac] represents an acetyl group at the N terminus, and [NH2] represents an amide at the C terminus.

In another embodiment nucleic acid molecules encoding any of the peptides of the invention are provided, as well as vectors comprising the nucleic acid sequence of a peptide of the invention.

In another embodiment a composition is provided comprising the single chain peptide of any of the foregoing embodiments, and a carrier, excipient or diluent.

In another embodiment, a method for treating cancer is provided comprising administering to a patient in need thereof an effective amount of the foregoing composition or a single chain peptide of any of the foregoing embodiments. In one embodiment, the cancer is acute lymphoblastic leukemia or acute lymphocytic leukemia, acute myeloid leukemia, or chronic myeloid leukemia (CML). In other embodiments, the cancer is lymphoma, small cell lung cancer, renal cell carcinoma, adenoid cystic carcinoma, squamous cell carcinoma of the head and neck, neuroblastoma, pancreatic cancer, follicular lymphoma, mantel cell lymphoma, breast cancer, uterine cancer, ovarian cancer, hepatocellular carcinoma, lung cancer, germ cell tumor, non-small cell lung cancer, gastric cancer, renal cancer, Kaposi's sarcoma, mesothelioma, desmoplastic small round cell tumor, Ewing sarcoma or lung adenocarcinoma.

These and other aspects of the invention will be understood from the following brief description of the figures and detailed description of the invention.

BRIEF DESCRIPTION OF THE FIGURES

FIG. 1a is a Molecular Dynamic Simulation modeling was performed to compare the molecular interactions within the native MYB:CBP complex to the interaction between a MYB peptide to CBP (L-amino acid peptide, labeled as L-aa (SEQ ID NO:2), and D-amino acid, labeled MYBMIM, SEQ ID NO:1, are compared here). FIG. 1b is a Microscale Thermopheresis (MST) to analyze the binding affinity of MYB peptides to the purified CBP-KIX domain. FIG. 1c shows the intranuclear penetration of FITC-labelled TAT peptides in MOLM13 cells using confocal microscopy. FIG. 1d is a Western blot showing specific binding of biotinylated-MYBMIM to CBP in MV411 human AML cells.

FIG. 2a is the quantification of live AML cells using Trypan blue exclusion after MYBMIM treatment. FIG. 2b shows induction of apoptosis observed with MYBMIM treatment of human AML cells. Flow cytometric analysis of Annexin-V and DAPI staining of MOLM13 cells after treatment with TG3 (20 μM) and MYBMIM (20 μM) for 24 hours. FIG. 2c shows that MYBMIM induces cell death without morphologic evidence of differentiation. FIG. 2d is a heatmap showing MYBMIM-induced gene expression changes in MOLM13 cells after 6 hour treatment with TG3 (20 μM) and MYBMIM (20 μM). FIG. 2e is a volcano plot of MYBMIM treated MV411 human AML cells compared to control. FIG. 2f shows BCL2 and MYC mRNA expression was measured by RT-qPCR and normalized to glyceraldehyde-3-phosphate dehydrogenase (GAPDH) expression. FIG. 2g shows ectopic expression of MSCV-Ires-GFP vector containing BCL2 in MV411 cells partially rescues MYBMIM-induced apoptosis, shown here by measurement of ATP activity using a CellTiter Glo luminescence assay.

FIG. 3a shows that MYBMIM has no significant effect on colony formation of CD34-enriched hematopoietic progenitor cells isolated from human umbilical cord blood and grown in growth-factor enriched semi-solid media. FIG. 3b shows white blood cell counts, measured in thousands/μL and FIG. 3c shows hemoglobin, measured in g/dL, n=5 for each treatment group. FIG. 3d shows the survival analysis of primary patient-derived MLL-rearranged leukemia cells (5×10^5 cells per mouse via tail vein injection) engrafted into sublethally irradiated immunodeficient mice and treated with MYB-MIM via intraperitoneal injection for 14 days (indicated as Treatment from days 3-17), p=0.0038.

FIGS. 4a-d show the activity of peptides of the invention against a panel of AML cell lines, and cell viability against MV411 cells. FIG. 4a shows SEQ ID NO:1 (MYBMIM) and FIG. 4b shows SEQ ID NO:25 (CRYBMIM) dosed at 10 and 20 μM every 48 hours for a 6 day period. FIG. 4c shows SEQ ID NO:1 and FIG. 4d shows SEQ ID NO:25 tested at 20 μM dose across a panel of AML cell lines and the results from day 6 of treatment

DETAILED DESCRIPTION OF THE INVENTION

Figure 1A:
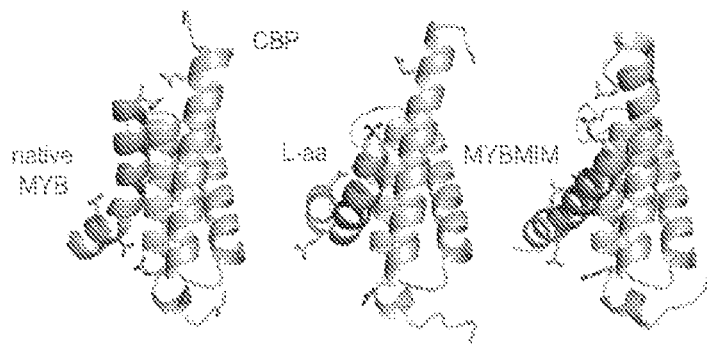
FIG. 1a-d show that a compound of the invention competes with the MYB:CBP complex in acute myeloid leukemia.

Despite recent efforts to improve stratification of conventional chemotherapy for the treatment of patients with acute myeloid leukemia (AML), cure rates remain poor. Recent genomic profiling studies have begun to reveal that AML is characterized by the predominance of mutations of genes encoding regulators of gene transcription and chromatin structure. Indeed, most AML chromosomal translocations, such as those involving MLL gene rearrangements, encode chimeric transcription or chromatin remodeling factors. Recent functional genomic efforts have identified specific molecular dependencies of aberrant AML gene expression, such as for example the requirement of DOT1L for the maintenance of MLL-rearranged leukemias, prompting the clinical development of DOT1L methyltransferase inhibitors for AML therapy. Similarly, additional AML subtypes appear dependent on aberrant gene expression, conferring a susceptibility to inhibition of CDK8 and BRD4 that regulate the Mediator transcriptional coactivator complex.

In addition to these established mechanisms, recent studies have also implicated aberrant activity of hematopoietic transcription factors and their coactivators, such as MYB and CREB-binding protein (CBP), in AML pathogenesis. In particular, MYB is a sequence-specific hematopoietic transcription factor that is required for the survival of AML1-ETO and MLL-rearranged leukemias. Transient suppression of MYB expression eliminates MLL-AF9 leukemias but is dispensable for normal myelopoiesis, emphasizing its specific functional requirements in AML pathogenesis. Leukemogenic activities of MYB requires its physical and specific association with the transcriptional co-activator CBP. This interaction is associated with recruitment of CBP and its chromatin remodeling of transcriptional circuits required for leukemogenesis. Indeed, Booreana mice mutant for Myb E308G that affects the molecular recognition of the KIX domain of CBP by MYB exhibit normal hematopoiesis, but are resistant to MLL-AF9-induced leukemogenesis.

Whereas previous attempts to interfere with aberrant transcriptional coactivation in AML have focused on pharmacologic blockade of CBP acetyltransferase activities, an alternative strategy is embodied herein to dismantle the assembly of the leukemogenic transcription factor-coactivator complex. The specific requirement of MYB E308 for molecular recognition of the CBP KIX domain was pursued. Using molecular mechanics simulations and structural analysis of the MYB:CBP molecular complex, stabilized, cell-penetrant peptidomimetic inhibitors of MYB:CBP binding were created. Consequently, their molecular and cellular activities, mechanisms of transcriptional regulation, and therapeutic activities in preclinical leukemia models in vitro and in vivo were investigated. These studies also support use of the same or similar strategy in treatment of any cancers in which MYB:CBP interaction leading to cancer is undesirable.

In one embodiment, peptides of the invention comprise a single chain amino acid sequence comprising two sequences: one sequence derived from the HIV-TAT protein, which allows for cell membrane penetration, and the other sequence is an amino acid sequence derived from MYB, said MYB sequence capable of interacting with and interfering with the MYB:CBP interface to prevent downstream activity of MYB:CBP such as that leading to, for example, leukemogenesis, described elsewhere herein. The TAT amino acid sequence and the MYB amino sequence on the single chain peptide may be separated by an amino acid linker sequence. The TAT sequence may be located at the N-terminal part of the single chain amino acid sequence and the MYB sequence at the C-terminal part, or they may be in the opposite positions, i.e., TAT at the C-terminal part and MYB at the N-terminal part. The single chain peptide may be comprised of L-amino acids, the conventional forms of amino acids comprising most naturally-occurring peptides and proteins. Alternatively, the single chain peptide may comprise D-amino acids, and the order of amino acids in the sequence reversed from that of a peptide containing L-amino acids, forming a "retro-inverso" form of the peptide, that retains the conformation and biological activities of the L-amino acid sequence, but is resistant to proteolysis in vivo. The ends of the single chain peptide may be modified, such as but not limited to acetylation of the amino terminus and an amide present at the carboxy terminus. The start and stop amino acid in a description herein refers to the amino acids positions in the L-amino acid sequence of the protein.

In one embodiment, the single-chain peptide comprises the TAT sequence at the N-terminal part (the orientation when the peptide comprises L-amino acids) and the MYB sequence at the C-terminal part. In the corresponding retro-inverso sequence, the D-amino acid reversed order TAT portion is at the C-terminus, and the D-amino acid, reversed order MYB portion at the N-terminus. Such orientation of the TAT and MYB portions, in one embodiment, provide an increased biological activity of the single-chain peptide by better interfering with assembly of the MYB-CBP complex, reducing transactivation and thus negatively affecting downstream gene regulation that would otherwise lead to dysregulation of gene transcription and triggering leukemic cell growth. Furthermore, the TAT and MYB sequences within the single chain peptide may each independently be in the L-amino acid or D-amino acid/reversed (i.e., retro-inverso) orientations, with or without a linker between the sequences. In one embodiment the linker comprises one or more amino acids, such as GG.

In one embodiment, peptides of the invention comprise a single chain amino acid sequence comprising three sequences: one sequence derived from the HIV-TAT protein, which allows for cell membrane penetration, one sequence from the CREB protein, capable of interacting with CBP, and one sequence is an amino acid sequence derived from MYB, said MYB sequence capable of interacting with and interfering with the MYB:CBP interface to prevent downstream activity of MYB:CBP such as that leading to, for example, leukemogenic, described elsewhere herein. The cell penetrating peptide sequence from TAT and the CBP binding peptide sequence from CREB may be separated by an amino acid linker sequence. The CBP binding peptide sequence from CREB and the CBP binding peptide sequence from MYB on the single chain peptide may be separated by a linker. In one embodiment, the linker is GG. The cell penetrating peptide sequence from TAT may be located at the N-terminal part of the single chain amino acid sequence and the MYB sequence at the C-terminal part, or they may be in the opposite positions, i.e., the cell penetrating peptide sequence from TAT at the C-terminal part and the CBP binding peptide sequence MYB at the N-terminal part. In one embodiment the linker comprises one or more amino acids, such as GG.

The single chain peptide may be comprised of L-amino acids, the conventional forms of amino acids comprising most naturally-occurring peptides and proteins, or the single chain peptide may comprise D-amino acids, and the order of amino acids in the sequence reversed, forming a "retro-inverso" form of the peptide, that retains the conformation and biological activities of the L-amino acid sequence, but is resistant to proteolysis in vivo. The ends of the single chain peptide may be modified, such as but not limited to acetylation of the amino terminus and an amide at the carboxy terminus. As will be noted below, each of the sequences from HIV-TAT, CREB, and MYB may be present in the single chain peptide independently as an L-amino acid sequence or a D-amino acid sequence in the reverse order of amino acids compared to the L-amino acid sequence.

In one embodiment, as noted above, the single-chain peptide of L-amino acids comprises the cell penetrating peptide sequence from TAT at the N-terminal part and the MYB sequence at the C-terminal part, and the CREB sequence in between. In the corresponding retro-inverso sequence, the retro-inverso cell penetrating peptide from TAT sequence is at the C-terminus, and the retro-inverso CBP binding peptide sequence of MYB is at the N-terminus, and the retro-inverso CBP binding peptide sequence from CREB is between them. Such orientation of the "TAT", "CREB" and "MYB" portions, in one embodiment, provide an increased biological activity of the single-chain peptide by better interfering with assembly of the MYB-CBP complex, reducing transactivation and thus negatively affecting downstream gene regulation that would otherwise lead to dysregulation of gene transcription and triggering leukemic cell growth. Furthermore, the "TAT", "CREB" and "MYB" sequences within the single chain peptide may, as noted herein, each independently be in the L-amino acid or D-amino acid/reversed (i.e., retro-inverso) orientations, with or without a linker between each sequence.

In another embodiment of the invention, modifications of one or more amino acids in a single-chain peptide may be made, to retain or even enhance the biological activity. In one embodiment, one or more amino acids may be conservatively substituted. In another embodiment one or more amino acids may be non-conservatively substituted. In such substitutions, amino acids substitutions are possible provided that these do not excessively affect the biological activity of the peptide. In one embodiment the substitutions enhance biological activity.

As is well-known in the art, a "conservative substitution" of an amino acid or a "conservative substitution variant" of a peptide refers to an amino acid substitution which maintains: 1) the secondary structure of the peptide; 2) the charge or hydrophobicity of the amino acid; and 3) the bulkiness of the side chain or any one or more of these characteristics. Illustratively, the well-known terminologies "hydrophilic residues" relate to serine or threonine. "Hydrophobic residues" refer to leucine, isoleucine, phenylalanine, valine or alanine, or the like. "Positively charged residues" relate to lysine, arginine, ornithine, or histidine. "Negatively charged residues" refer to aspartic acid or glutamic acid. Residues having "bulky side chains" refer to phenylalanine, tryptophan or tyrosine, or the like. A list of illustrative conservative amino acid substitutions is given below (amino acids are L-amino acids unless indicated with "D-"). The symbol pS represents phosphoserine.

| For Amino Acid (3- and 1-Letter Codes) | Replace With |
| --- | --- |
| Alanine (Ala, A) | D-Ala, Gly, 2-aminoisobutyrate, β-Ala, L-Cys, D-Cys |
| Arginine (Arg, R) | D-Arg, Lys, D-Lys, Orn D-Orn, Propylguanidine |
| Asparagine (Asn, N) | D-Asn, Asp, D-Asp, Glu, D-Glu, Gln, D-Gln |
| Aspartic Acid (Asp, D) | D-Asp, D-Asn, Asn, Glu, D-Glu, Gln, D-Gln |
| Cysteine (Cys, C) | D-Cys, S-Me-Cys, Met, D-Met, Thr, D-Thr |
| Glutamine (Glu, Q) | D-Gln, Asn, D-Asn, Glu, D-Glu, Asp, D-Asp |
| Glutamic Acid (Glu, E) | D-Glu, D-Asp, Asp, Asn, D-Asn, Gln, D-Gln, Carboxyglutamate, Butyrate |
| Glycine (Gly, G) | Ala, D-Ala, Pro, D-Pro, Aib, β-Ala |
| Histidine (His, H) | D-His, D-Asn, Asn, D-Gln, Gln, D-Lys, L ys, D-Arg, Arg |
| Isoleucine (Ile, I) | D-Ile, Val, D-Val, Leu, D-Leu, Met, D-Met |
| Leucine (Leu, L) | Val, D-Val, Met, D-Met, D-Ile, D-Leu, Ile, Norleucine, Tert-Leucine |
| Lysine (Lys, K) | D-Lys, Arg, D-Arg, Orn, D-Orn |
| Methionine (Met, M) | D-Met, S-Me-Cys, He, D-Ile, Leu, D-Leu, Val, D-Val |
| Phenylalanine (Phe, F) | D-Phe, Tyr, D-Tyr, His, D-His, Trp, D-Trp |
| Proline (Pro, P) | D-Pro |
| Serine (Ser, S) | D-Ser, Thr, D-Thr, allo-Thr, L-Cys, D-Cys |
| Threonine (Thr, T) | D-Thr, Ser, D-Ser, allo-Thr, Met, D-Met, Val, D-Val |
| Tryptophan (Trp, W) | D-Trp, D-Tyr, Tyr, D-Phe, Phe |
| Tyrosine (Tyr, Y) | D-Tyr, Phe, D-Phe, His, D-His, Trp, D-Trp |
| Valine (Val, V) | D-Val, Leu, D-Leu, Ile, D-Ile, Met, D-Met |

In one embodiment, conservative side chain substitutions, such as L-I-V, S-C-T, E-D, N-Q and K-R, can be used to obtain analogues of any of the single chain peptides embraced herein or their comprising sequences from TAT and MYB, or from TAT, CREB and MYB.

Linkers optionally between any sequence in a single chain peptide of the invention may comprise one or more amino acids or a non-amino acid. In one embodiment the linker is a sequence of one to about 8 glycines. In one embodiment the linker is two glycines (GG).

The single chain peptide of the invention may be one of those sequences described herein, or may have one amino acid changed among those described herein. In another embodiment, the peptide may have two one amino acids changed among those described herein. In another embodiment, the peptide may have three one amino acids changed among those described herein. In another embodiment, the peptide may have four one amino acids changed among those described herein. In another embodiment, the peptide may have five or more one amino acids changed among those described herein. The foregoing number of changes may appy to the single chain peptide or any one or more of the sequences from TAT or MYB, or from TAT, CREB or MYB, contained therein. In one embodiment, the peptide sequence of TAT, MYB or CREB may have ≥98% sequence homology with a respective peptide described herein. In one embodiment, the peptide may have ≥95% sequence homology with a peptide described herein. In one embodiment, the peptide may have ≥90% sequence homology with a peptide described herein. In one embodiment, the peptide may have ≥85% sequence homology with a peptide described herein. In one embodiment, the peptide may have ≥80% sequence homology with a peptide described herein. In one embodiment, the peptide may have ≥75% sequence homology with a peptide described herein. In one embodiment, the peptide may have ≥70% sequence homology with a peptide described herein. In the foregoing embodiments, the peptide retains one or more biological activities described herein, or one or more activities are enhanced.

In another embodiment, deletions, truncations, additions, or other modifications of the single chain peptide may be made, that retain or even enhance the biological activity. One or more amino acids may be added, deleted, including truncation of one or both ends of either the "TAT" and "MYB" portions of the peptide in one embodiment, or in the "TAT", "CREB" or "MYB" portions of the peptide in another embodiment.

In another embodiment, the peptide may comprise both L-amino acids and D-amino acids, such that the peptide retains or has even enhanced biological activity.

Biological activity means any one or more of the activities of peptides described herein, such as but not limited to cell penetration, competition with MYB:CBP interaction, interfering with MYB:CBP interaction, reducing downstream activity from MYB:CBP interaction, downregulation of MYB-regulated genes, downregulation of MYC, downregulation of BCL2, inducing apoptosis in leukemic cells in vitro, anti-leukemic activity in vivo, and any combination of any of the foregoing.

In one embodiment, the portion of the cell penetrating peptide sequence from HIV-TAT in the single chain peptide of the invention comprises the L-amino acids YGRKKRRQRRR (SEQ ID NO:16). In a retro-inverso single chain peptide or retro-inverso portion thereof, the sequence is the D-amino acids RRRQRRKKRGY (SEQ ID NO:17). In one embodiment, the portion of the MYB sequence that a single chain peptide of the invention comprises the L-amino acids KRIKELELLLMSTENELK (SEQ ID NO:18) which are amino acids 293-310 of human MYB. In a retro-inverso single chain peptide, or a retro-inverso portion thereof, the sequence is the D-amino acids KLENETSMLLLELEKIRK (SEQ ID NO:19). Corresponding MYB sequences from other mammalian species are also embraced by this invention. As will be discussed below, in other embodiments, a fragment of either the cell penetrating peptide sequence from TAT, a fragment of the CBP binding peptide sequence from MYB, or both, may be present in the single-chain peptide of the invention. Fragment refers to a contiguous portion of the full-length sequences, truncated at one or both ends. The fragment retains the biological activity of the full peptide sequence.

In one embodiment, the portion of the cell penetrating peptide sequence from HIV-TAT in the single chain peptide of the invention comprises the L-amino acids YGRKKRRQRRR (SEQ ID NO:16). In a retro-inverso single chain peptide or retro-inverso portion thereof, the sequence is the D-amino acids RRRQRRKKRGY (SEQ ID NO:17). In one embodiment, the portion of the MYB sequence that a single chain peptide of the invention comprises the L-amino acids LELLLMSTENELK (SEQ ID NO:21) which are amino acids 298-310 of human MYB. In a retro-inverso single chain peptide, or a retro-inverso portion thereof, the sequence is the D-amino acids KLENETSMLLLEL (SEQ ID NO:24). In one embodiment a linker, such as GG, may be disposed between the sequences. In one embodiment, the N-terminal amino acid may have an acetyl group, the C-terminus have an amide group, or both. Thus, the single chain, L-amino acid peptide YGRKKRRQRRGGLELLLMSTENELK (SEQ ID NO:38) and the single chain D-amino acid peptide LELLLMSTENELKGGRRRQRRKKRGY (SEQ ID NO:39), and their N-acetyl and C-amide analogues, are embraced herein.

In one embodiment, SEQ ID NO:1 (which also may be referred to herein as MYBMIM) and SEQ ID NO:2 (which also may be referred to herein as TATMYB) were developed in order to interfere with the assembly of the molecular MYB: CBP complex at micromolar concentrations and rapidly accumulate in the nuclei of AML cells. As will be seen in the examples herein, treatment of AML cells with SEQ ID NO:1, but not with its inactive near-isosteric analogue SEQ ID NO:3 (which also may be referred to herein as TG3), led to the displacement and dissociation of MYB:CBP complex in cells, causing rapid downregulation of MYB-dependent gene expression including MYC and BCL2 oncogenes. As also will be seen in the examples below, this was associated with obliteration of H3K27Ac-driven oncogenic enhancers induced by CBP and enriched for MYB binding sites. Both human MLL-rearranged and non-rearranged AML cells, but not normal CD34+ umbilical cord blood progenitor cells, underwent sustained mitochondrial apoptosis in response to SEQ ID NO:1 treatment, an effect that could be partially blocked by ectopic expression of BCL2. Treatment using 50 mg/kg/day SEQ ID NO:1 impeded leukemia progression and extended survival of immunodeficient mice engrafted with primary patient-derived MLL-rearranged leukemia cells. These findings demonstrate the dependence of human AML on MYB:CBP transcriptional dysregulation, and establishes a pharmacologic approach for its therapeutic blockade following the teachings herein.

In one embodiment, an MYB site was identified amenable to therapeutic blockade using cell permeable peptidomimetic molecules. In one embodiment, a cell permeable peptidomimetic inhibitor of the MYB:CBP interface combines the HIV-TAT protein transduction domain with the interacting domain of MYB to CBP. The peptide may be made in a retro-inverso conformation with D-amino acids with the goal of maintaining helical geometry of the peptide structure while protecting it from intracellular proteolysis. The activity of this peptide was compared to that of a variant of the peptide (SEQ ID NO:3) which includes three glycine amino acid substitutions at the MYB 294, 302, and 308 positions, thus substituting a small chain amino acid at the three sites in MYB that create the important charged (294, 308 positions) and hydrophobic (302) interactions between MYB and CBP. The SEQ ID NO:3 peptide is ultimately unable to interact with CBP and as a consequence, is rendered inactive.

Thus, in one embodiment, peptides comprising L-amino acids or D-amino acids (the latter typically in a retro-inverso configuration of the corresponding L-amino acid sequence) are provided that interact with and reduce or prevent downstream MYB:CBP activity, downregulate MBY-regulated genes and kill leukemic cells in vivo. In one embodiment, the peptide consists of D-amino acids and is acetyl-KLENETSMLLLELEKIRKGGRRRQRRKKRGY-NH$_2$ (SEQ ID NO:1). In another embodiment the peptide consists of L-amino acids and is acetyl-YGRKKRRQRRRGGKRIKELELLLMSTENELK-NH$_2$ SEQ ID NO:2). In one embodiment, the peptide consisting of D-amino acids is KLENETSMLLLELEKIRKG-GRRRQRRKKRGY (SEQ ID NO:7). In another embodiment the peptide consisting of L-amino acids is YGRKKRRQRRRGGKRIKELELLLMSTENELK SEQ ID NO:8). In other embodiments, the peptide may be modified at the amino terminal or carboxy terminal ends. In one embodiment, the amino terminal end is acetylated. In another embodiment the carboxy terminal end is an amide. As noted above, both SEQ ID NO:1 and SEQ ID NO:2 have an amino terminal acetyl group and a carboxy terminal amide.

Various modifications of these peptides may be made for studying the cell penetration and other biological activities of the peptides. In one embodiment, an inactive form of SEQ ID NO:1 is provided wherein glycines are present at the 294, 302 and 308 positions of the MYB sequence therein, providing the D-amino acid peptide [Ac]-KLGNETSMGL-LELEKIGKGG-RRRQRRKKRGY-[NH2] (SEQ ID NO:3). In another embodiment, a biotin moiety is coupled to the amino terminal portion of SEQ ID NO:2, providing D-amino acid peptide Biotin-YGRKKRRQRRRGGKRIKELELLLMSTENELK-NH$_2$ (SEQ ID NO:4; may be referred to herein as BIOMYB). In another embodiment a biotin moiety is coupled to the carboxy terminal portion of SEQ ID NO:1 via a carboxy terminal lysine, which is also an amide, providing D-amino acids acetyl-KLENETSMLLLELEKIRKG-GRRRQRRKKRGYK-biotin-NH$_2$ (SEQ D NO:5; may be referred to herein as RI-BIOMYB). In other experiments, a fluorescein-conjugated TAT peptide is provided, using fluorescein isothiocyanate and aminohexanoic acid at the amino terminus and amide at the carboxy terminus, L-amino acids FITC-AHA-YGRKKRRQRRR-NH2, SEQ ID NO:6 (may be referred to herein as FITC-TAT; FITC representing fluorescein isothiocyanate and AHA representing aminohexanoic acid, the fluorophore and linker moieties, respectively). In another embodiment a fluorescein-conjugated retro-inverso MYB peptide is provided, D-amino acids FITC-AHA-KLENETSMLLLELEKIRK-NH$_2$ (SEQ ID NO:9).

As noted above, various modifications of the aforementioned peptides may be carried out while preserving the biological activity of the peptide for its intended purposes. By way of non-limiting example, the peptides SEQ ID NO:2 and 8, which are comprised of L-amino acids, may be provided in retro-inverso configurations to protect against proteolytic degradation in vivo; in such a configuration, D-amino acids are used and the sequence is inverted, thus providing the identical orientation of the pendant side groups of the amino acids, SEQ ID Nos: 1 and 7, respectively. Chemical modifications of the amino and carboxy termini are embodied herein, such as but not limited to, acetylation at the N terminus, amide formation at the C terminus, or both.

In one embodiment, the modifications described for the single-chain peptide comprising "TAT" and "MYB" above are applicable to a single chain peptide comprising "TAT", "CREB" and "MYB", as described further described below.

In one embodiment, the invention is directed to a single chain peptide comprising a cell penetrating peptide sequence from HIV-TAT, a CBP binding peptide sequence from CREB, and a CBP binding peptide sequence from MYB. In one embodiment, the sequence in the single chain peptide from HIV-TAT is L-amino acid sequence YGRKKRRQRRR (SEQ ID NO:16). In one embodiment, the sequence of the CBP binding peptide sequence from CREB is the L-amino acid sequence RREILSRRPpSYRK (SEQ ID NO:20), and the sequence in the single chain peptide from MYB is L-amino acid sequence LELLLMSTENELK (SEQ ID NO:21). In one embodiment, the cell penetrating peptide sequence from HIV-TAT and the CBP binding peptide sequence from CREB are joined by a linker. In one embodiment, the linker is GG. The CBP binding peptide from MYB and the CBP binding peptide from CREB may also be joined by a linker.

In one embodiment, the cell penetrating peptide sequence from HIV-TAT, the CBP binding protein sequence from CREB and the CBP binding peptide sequence from MYB in the single chain peptide are composed of L-amino acids. In one embodiment the N-to-C order of sequences is TAT-CREB-MYB. In one embodiment, the single chain peptide has the L-amino acid sequence YGRKKRRQRRRGGR-REILSRRPpSYRKLELLLMSTENELK (SEQ ID NO:22).

In one embodiment, the cell penetrating peptide sequence from HIV-TAT, the CBP binding protein sequence from CREB, and the CBP binding peptide sequence from MYB are composed of D-amino acids, and the order of amino acids in each sequence is inverted from that of the L-amino acid sequence (i.e., retro-inverso). In one embodiment, the sequence from HIV-TAT is the D-amino acid sequence RRRQRRKKRGY (SEQ ID NO:17). In one embodiment the sequence from CREB is the D-amino acid sequence KRYpSPRRSLIERR (SEQ ID NO:23). In one embodiment, the sequence from MYB is the D-amino acid sequence KLENETSMLLLEL (SEQ ID NO:24). In one embodiment, the N-to-C order of the retro-inverso sequences is MYB-CREB-TAT. In one embodiment, the single chain peptide has the D-amino acid sequence KLENETSMLL-LELKRYpSPRRSLIERRGGRRRQRRKKRGY (SEQ ID NO:25).

In one embodiment, each of the cell penetrating peptide sequence from HIV-TAT, the CBP binding peptide sequence from CREB, and the CBP binding peptide sequence from MYB peptide, or two or three of these sequences within the single chain peptide, comprises one or more amino acid additions, deletions or substitutions, or the N-terminus is acetylated, the C-terminus is amidated, or any combination thereof. Substitutions include conservative or non-conservative substitutions. In one embodiment, each of the cell penetrating peptide sequence from HIV-TAT, the CBP binding peptide sequence from CREB, the CBP binding peptide sequence from MYB, or two or three of these sequences within the single chain peptide independently has at least 98%, at least 95%, at least 90%, at least 85%, at least 80% or at least 75% sequence identity with the respective fragment of the HIV-TAT, CREB, and MYB sequences within SEQ ID NOS: 16, 20 and 18, respectively. Furthermore, the single chain peptide of this embodiment may comprise longer or shorter fragments of the three respective components, as further described below. The aforementioned embodiments apply to either the L-amino acid or D-amino acid/reversed sequences of the invention.

In another embodiment, the cell penetrating peptide sequence from the TAT component of the single-chain peptide may be any fragment of L-amino acids (SEQ ID NO:28). In another embodiment, the CREB component of the single-chain peptide may be any fragment of L-amino acids 124-146 of CREB, RREILSRRPpSYRKILNDLSSDAP (SEQ ID NO:29). In one embodiment, the fragment of the CBP binding peptide sequence of CREB is L-amino acids 133-146, pSYRKILNDLSSDAP (SEQ ID NO:30). In one embodiment, the fragment of the CBP binding peptide sequence of CREB is L-amino acids 133-139, pSYRKILN (SEQ ID NO: 37). In one embodiment, the CBP peptide binding fragment of MYB is L-amino acids 293-310, KRIKELELLLMSTENELK (SEQ ID NO:18). In another embodiment, the fragment of CBP binding peptide of MYB is L-amino acids 298-310, LELLLMSTENELK (SEQ ID NO:21). In another embodiment the fragment of MYB is L-amino acids 302-309, LMSTENEL (SEQ ID NO:31). In another embodiment, conservative side chain substitutions, such as L-I-V, S-C-T, E-D, N-Q and K-R can be used to obtain analogues.

If the component of the above fragment is in the D-amino acid and reversed order (retro inverso format), the corresponding peptides are: cell penetrating peptide from TAT component of the single-chain peptide may be any fragment of D-amino acids (SEQ ID NO:17). In another embodiment, the CBP binding peptide from CREB component of the single-chain peptide may be any fragment of D-amino acids 124-146 of CREB, PADSSLDNLIKRYpSPRRSLIERR (SEQ ID NO:33). In one embodiment, the fragment of CREB is D-amino acids 133-146, PADSSLDNLIKRYpS (SEQ ID NO:34). In one embodiment, the fragment of CREB is D-amino acids 133-139, NLIKRYpS (SEQ ID NO:36). In one embodiment, the fragment of MYB is D-amino acids 293-310, KLENETSMLLLELEKIRK (SEQ ID NO:19). In another embodiment the fragment of MYB is D-amino acids 302-309, LENETSML (SEQ ID NO:35). As noted above, fragment refers to a continuous sequence of amino acids from within the peptide, which can be truncated at either the N- or C-terminus or both, and retains the desired activity of the peptide. Furthermore, as noted above, the amino acid ranges denoted for each sequence are that from the respective peptide in the L-amino acid, then provided as D-amino acids in the reverse order in the single chain peptide or D-amino acid portion thereof. In another embodiment, conservative side chain substitutions, such as the D-amino acid isomers of L-I-V, S-C-T, E-D, N-Q and K-R can be used to obtain analogues.

Thus, in one embodiment, wherein the single chain peptide is comprised entirely of L-amino acids, the N-terminal portion is amino acids 47-57 of the cell penetrating peptide sequence from HIV-TAT, L-amino acids YGRKKRRQRRR (SEQ ID NO:16); the C-terminal portion is amino acids 298-310 of the CBP binding peptide from MYB, L-amino acids LELLLMSTENELK (SEQ ID NO:21), and between them, amino acids 124-136 the CBP binding peptide sequence from CREB, L-amino acids RREILSRRPpSYRK (SEQ ID NO:20). In one embodiment, the sequences from HIV-TAT and from CREB are joined by a linker. In one embodiment the linker is GG.

Thus, in one embodiment, wherein the single chain peptide is comprised entirely of L-amino acids, the N-terminal portion is amino acids 47-57 the cell penetrating peptide sequence from HIV-TAT, L-amino acids YGRKKRRQRRR (SEQ ID NO:16); the C-terminal portion is amino acids 293-310 of the CBP binding peptide from MYB, L-amino acids KRIKELELLLMSTENELK (SEQ ID NO:18), and between them, amino acids 124-136 the CBP binding peptide sequence from CREB, L-amino acids RREILSRRPpSYRK (SEQ ID NO:20). In one embodiment, the sequences from HIV-TAT and from CREB are joined by a linker. In one embodiment the linker is GG.

Thus, in one embodiment, wherein the single chain peptide is comprised entirely of L-amino acids, the N-terminal portion is amino acids 47-57 of the cell penetrating peptide sequence from HIV-TAT, L-amino acids YGRKKRRQRRR (SEQ ID NO:16); the C-terminal portion is amino acids 302-309 of the CBP binding peptide from MYB, L-amino acids LMSTENELK (SEQ ID NO:31), and between them, amino acids 124-136 the CBP binding peptide sequence from CREB, L-amino acids RREILSRRPpSYRK (SEQ ID NO:20). In one embodiment, the sequences from HIV-TAT and from CREB are joined by a linker. In one embodiment the linker is GG.

Thus, in one embodiment, wherein the single chain peptide is comprised entirely of L-amino acids, the N-terminal portion is amino acids 47-57 of the cell penetrating peptide sequence from HIV-TAT, L-amino acids YGRKKRRQRRR (SEQ ID NO:16); the C-terminal portion is amino acids 298-310 of the CBP binding peptide from MYB, L-amino acids LELLLMSTENELK (SEQ ID NO:21), and between them, amino acids 133-146 the CBP binding peptide sequence from CREB, L-amino acids pSYRKILNDLSSDAP (SEQ ID NO:30). In one embodiment, the sequences from HIV-TAT and from CREB are joined by a linker. In one embodiment the linker is GG.

Thus, in one embodiment, wherein the single chain peptide is comprised entirely of L-amino acids, the N-terminal portion is amino acids 47-57 of the cell penetrating peptide sequence from HIV-TAT, L-amino acids YGRKKRRQRRR (SEQ ID NO:16); the C-terminal portion is amino acids 302-309 of the CBP binding peptide from MYB, L-amino acids LMSTENELK (SEQ ID NO:31), and between them, amino acids 133-146 the CBP binding peptide sequence from CREB, L-amino acids pSYRKILNDLSSDAP (SEQ ID NO:30). In one embodiment, the sequences from HIV-TAT and from CREB are joined by a linker. In one embodiment the linker is GG.

Thus, in one embodiment, wherein the single chain peptide is comprised entirely of L-amino acids, the N-terminal portion is amino acids 47-57 of the cell penetrating peptide sequence from HIV-TAT, L-amino acids YGRKKRRQRRR (SEQ ID NO:16); the C-terminal portion is amino acids 293-310 of the CBP binding peptide from MYB, L-amino acids KRIKELELLLMSTENELK (SEQ ID NO:18), and between them, amino acids 124-136 the CBP binding peptide sequence from CREB, L-amino acids RREILSRRPpSYRK (SEQ ID NO:20). In one embodiment, the sequences from HIV-TAT and from CREB are joined by a linker. In one embodiment the linker is GG.

Thus, in one embodiment, wherein the single chain peptide is comprised entirely of L-amino acids, the N-terminal portion is amino acids 47-57 of the cell penetrating peptide sequence from HIV-TAT, L-amino acids YGRKKRRQRRR (SEQ ID NO:16); the C-terminal portion is amino acids 298-310 of the CBP binding peptide from MYB, L-amino acids LELLLMSTENELK (SEQ ID NO:21), and between them, amino acids 133-139 the CBP binding peptide sequence from CREB, L-amino acids pSYRKILN (SEQ ID NO:37). In one embodiment, the sequences from HIV-TAT and from CREB are joined by a linker. In one embodiment the linker is GG.

Thus, in one embodiment, wherein the single chain peptide is comprised entirely of L-amino acids, the N-terminal portion is amino acids 47-57 of the cell penetrating peptide sequence from HIV-TAT, L-amino acids YGRKKRRQRRR (SEQ ID NO:16); the C-terminal portion is amino acids 293-310 of the CBP binding peptide from MYB, L-amino acids KRIKELELLLMSTENELK (SEQ ID NO:18), and between them, amino acids 133-139 the CBP binding peptide sequence from CREB, L-amino acids pSYRKILN (SEQ ID NO:37). In one embodiment, the sequences from HIV-TAT and from CREB are joined by a linker. In one embodiment the linker is GG.

Thus, in one embodiment, wherein the single chain peptide is comprised entirely of L-amino acids, the N-terminal portion is amino acids 47-57 of the cell penetrating peptide sequence from HIV-TAT, L-amino acids YGRKKRRQRRR (SEQ ID NO:16); the C-terminal portion is amino acids 302-309 of the CBP binding peptide from MYB, L-amino acids LMSTENELK (SEQ ID NO:31), and between them, amino acids 133-139 the CBP binding peptide sequence from CREB, L-amino acids pSYRKILN (SEQ ID NO:37). In one embodiment, the sequences from HIV-TAT and from CREB are joined by a linker. In one embodiment the linker is GG.

Thus, in one embodiment, wherein the single chain peptide is comprised entirely of D-amino acids, and the order of amino acids reversed from that in the corresponding L-amino acid sequence (i.e., retro-inverso), the N-terminal portion is amino acids 298-310 of the CBP binding peptide from MYB, D-amino acids KLENETSMLLLEL (SEQ ID NO:24), the C-terminal portion is amino acids 47-57 of the cell penetrating peptide sequence from HIV-TAT, D-amino acids RRRQRRKKRGY (SEQ ID NO:17); and between them, amino acids 124-136 the CBP binding peptide sequence from CREB, D-amino acids KRYpSPRRSLIERR (SEQ ID NO:23). In one embodiment, the sequences from HIV-TAT and from CREB are joined by a linker. In one embodiment the linker is GG.

Thus, in one embodiment, wherein the single chain peptide is comprised entirely of D-amino acids, and the order of amino acids reversed from that in the corresponding L-amino acid sequence (i.e., retro-inverso), the N-terminal portion is amino acids 293-310 of the CBP binding peptide from MYB, D-amino acids KLENETSMLLLELEKIRK (SEQ ID NO:19), the C-terminal portion is amino acids 47-57 of the cell penetrating peptide sequence from HIV-TAT, D-amino acids RRRQRRKKRGY (SEQ ID NO:17); and between them, amino acids 133-146 the CBP binding peptide sequence from CREB, D-amino acids PADSSLDN-LIKRYpS (SEQ ID NO:34). In one embodiment, the sequences from HIV-TAT and from CREB are joined by a linker. In one embodiment the linker is GG.

Thus, in one embodiment, wherein the single chain peptide is comprised entirely of D-amino acids, and the order of amino acids reversed from that in the corresponding L-amino acid sequence (i.e., retro-inverso), the N-terminal portion is amino acids 293-310 of the CBP binding peptide from MYB, D-amino acids KLENETSMLLLELEKIRK (SEQ ID NO:19), the C-terminal portion is amino acids 47-57 of the cell penetrating peptide sequence from HIV-TAT, D-amino acids RRRQRRKKRGY (SEQ ID NO:17); and between them, amino acids 124-146 the CBP binding peptide sequence from CREB, D-amino acids KRYpSPRRSLIERR (SEQ ID NO:23). In one embodiment, the sequences from HIV-TAT and from CREB are joined by a linker. In one embodiment the linker is GG.

Thus, in one embodiment, wherein the single chain peptide is comprised entirely of D-amino acids, and the order of amino acids reversed from that in the corresponding L-amino acid sequence (i.e., retro-inverso), the N-terminal portion is amino acids 302-309 of the CBP binding peptide from MYB, D-amino acids LENETSML (SEQ ID NO:35), the C-terminal portion is amino acids 47-57 of the cell penetrating peptide sequence from HIV-TAT, D-amino acids RRRQRRKKRGY (SEQ ID NO:17); and between them, amino acids 124-136 the CBP binding peptide sequence from CREB, D-amino acids KRYpSPRRSLIERR (SEQ ID NO:23). In one embodiment, the sequences from HIV-TAT and from CREB are joined by a linker. In one embodiment the linker is GG.

Thus, in one embodiment, wherein the single chain peptide is comprised entirely of D-amino acids, and the order of amino acids reversed from that in the corresponding L-amino acid sequence (i.e., retro-inverso), the N-terminal portion is amino acids 298-310 of the CBP binding peptide from MYB, D-amino acids KLENETSMLLLEL (SEQ ID NO:24), the C-terminal portion is amino acids 47-57 of the cell penetrating peptide sequence from HIV-TAT, D-amino acids RRRQRRKKRGY (SEQ ID NO:17); and between them, amino acids 133-146 the CBP binding peptide sequence from CREB, D-amino acids PADSSLDNLIKR-YpS (SEQ ID NO:34). In one embodiment, the sequences from HIV-TAT and from CREB are joined by a linker. In one embodiment the linker is GG.

Thus, in one embodiment, wherein the single chain peptide is comprised entirely of D-amino acids, and the order of amino acids reversed from that in the corresponding L-amino acid sequence (i.e., retro-inverso), the N-terminal portion is amino acids 302-309 of the CBP binding peptide from MYB, D-amino acids LENETSML (SEQ ID NO:35), the C-terminal portion is amino acids 47-57 of the cell penetrating peptide sequence from HIV-TAT, D-amino acids RRRQRRKKRGY (SEQ ID NO:17); and between them, amino acids 133-146 the CBP binding peptide sequence from CREB, D-amino acids PADSSLDNLIKRYpS (SEQ ID NO:34). In one embodiment, the sequences from HIV-TAT and from CREB are joined by a linker. In one embodiment the linker is GG.

Thus, in one embodiment, wherein the single chain peptide is comprised entirely of D-amino acids, and the order of amino acids reversed from that in the corresponding L-amino acid sequence (i.e., retro-inverso), the N-terminal portion is amino acids 293-310 of the CBP binding peptide from MYB, D-amino acids KLENETSMLLLELEKIRK (SEQ ID NO:19), the C-terminal portion is amino acids 47-57 of the cell penetrating peptide sequence from HIV-TAT, D-amino acids RRRQRRKKRGY (SEQ ID NO:17); and between them, amino acids 133-139 the CBP binding peptide sequence from CREB, D-amino acids NLIKRYpS (SEQ ID NO:36). In one embodiment, the sequences from HIV-TAT and from CREB are joined by a linker. In one embodiment the linker is GG.

Thus, in one embodiment, wherein the single chain peptide is comprised entirely of D-amino acids, and the order of amino acids reversed from that in the corresponding L-amino acid sequence (i.e., retro-inverso), the N-terminal portion is amino acids 298-310 of the CBP binding peptide from MYB, D-amino acids KLENETSMLLLEL (SEQ ID NO:24), the C-terminal portion is amino acids 47-57 of the cell penetrating peptide sequence from HIV-TAT, D-amino acids RRRQRRKKRGY (SEQ ID NO:17); and between them, amino acids 133-139 the CBP binding peptide sequence from CREB, D-amino acids NLIKRYpS (SEQ ID NO:36). In one embodiment, the sequences from HIV-TAT and from CREB are joined by a linker. In one embodiment the linker is GG.

Thus, in one embodiment, wherein the single chain peptide is comprised entirely of D-amino acids, and the order of amino acids reversed from that in the corresponding L-amino acid sequence (i.e., retro-inverso), the N-terminal portion is amino acids 302-309 of the CBP binding peptide from MYB, D-amino acids LENETSML (SEQ ID NO:35), the C-terminal portion is the cell penetrating peptide sequence from HIV-TAT, D-amino acids RRRQRRKKRGY (SEQ ID NO:17); and between them, amino acids 133-139 the CBP binding peptide sequence from CREB, D-amino acids NLIKRYpS (SEQ ID NO:36). In one embodiment, the sequences from HIV-TAT and from CREB are joined by a linker. In one embodiment the linker is GG.

In one embodiment, the single chain peptide has the L-amino acid sequence is [Ac]-YGRKKRRQRRRGGR-REILSRRPpSYRK-LELLLMSTENELK-[NH2] (SEQ ID NO:26) and in one embodiment, the single chain peptide has the D-amino acid sequence [Ac]-KLENETSMLL-LELKRYpSPRRSLIERRGGRRRQRRKKRGY-[NH2] (SEQ ID NO:27). In various embodiments, the N-terminus may be acetylated, the C-terminus amidated, or the combination of both.

In another embodiment nucleic acid molecules encoding any of the peptides of the invention are provided, as well as vectors comprising the nucleic acid sequence of a peptide of the invention. In another embodiment, the method entails introduction of the genetic sequence that encodes the peptides of this invention using, e.g., one or more nucleic acid delivery techniques. Nucleic acids of the invention include, in another embodiment, DNA, RNA and mixtures of DNA and RNA, alone or in conjunction with non-nucleic acid components. In another embodiment, the method comprises administering to the subject a vector comprising a polynucleotide sequence, which encodes a peptide of the present invention (Tindle, R. W. et al. Virology (1994) 200:54). In another embodiment, the method comprises administering to the subject naked DNA which encodes a peptide, or in another embodiment, two or more peptides of this invention (Nabel, et al. PNAS-USA (1990) 90: 11307). Each possibility represents a separate embodiment of the present invention. Moreover, nucleic acids encoding the single chain peptide may provide for facile synthesis or production of peptides for therapeutic use, by expression in any number of biological systems.

Nucleic acids can be administered to a subject via any means as is known in the art, including parenteral or intravenous administration, or in another embodiment, by means of a gene gun. In another embodiment, the nucleic acids are administered in a composition, which correspond, in other embodiments, to any embodiment listed herein.

Vectors for use according to methods of this invention can comprise any vector that facilitates or allows for the expression of a peptide of this invention. Vectors comprises, in some embodiments, attenuated viruses, such as vaccinia or fowlpox, such as described in, e.g., U.S. Pat. No. 4,722,848, incorporated herein by reference. In another embodiment, the vector is BCG (Bacille Calmette Guerin), such as described in Stover et al. (Nature 351:456-460 (1991)). A wide variety of other vectors useful for therapeutic administration or immunization of the peptides of the invention, e.g., *Listeria, Salmonella typhi* vectors, and the like, will be apparent to those skilled in the art from the description herein.

Pharmaceutical Compositions

As discussed above, this invention provides novel compounds that have biological properties useful for the treatment of any of a number of conditions or diseases in which interfering with MYB:CBP interactions have a therapeutically useful role.

The compounds and compositions of the invention may be administered to a subject or patients by any suitable route. Such routes include but are not limited to parenterally, such as intravenously, subcutaneously, intradermally, intramucosally; topically; orally; intraocularly, intracamerally, or by inhalation. Depending on the location of the cancer to be treated, the compound or composition of the invention may be delivered in or near the site.

Accordingly, in another aspect of the present invention, pharmaceutical compositions are provided, which comprise any one or more of the compounds described herein (or a prodrug, pharmaceutically acceptable salt or other pharmaceutically acceptable derivative thereof), and optionally comprise a pharmaceutically acceptable carrier, diluent or excipient. In certain embodiments, these compositions optionally further comprise one or more additional therapeutic agents. Alternatively, a compound of this invention may be administered to a patient in need thereof in combination with the administration of one or more other therapeutic agents. For example, additional therapeutic agents for conjoint administration or inclusion in a pharmaceutical composition with a compound of this invention may be an approved agent to treat the same or related indication, or it may be any one of a number of agents undergoing approval in the Food and Drug Administration that ultimately obtain approval for the treatment of any disorder related to cancer. It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a pro-drug or other adducts such as carrier proteins, fatty acids, dyes or polymers, or derivative of a compound of this invention which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in J. Pharmaceutical Sciences, 66: 1-19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Additionally, as used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkalotic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Liquid dosage forms for oral administration include, but are not limited to, pharmaceutically acceptable emulsions, micro emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut (peanut), corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly(orthoesters) and poly(anhydrides). Depot injectable formulations are also prepared by entrapping the drug in liposomes or microemulsions which are compatible with body tissues.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

In other embodiments solid dosage forms are provided. In certain embodiments, such solid dosage forms provide a higher than about a 20% oral bioavailability. As will be shown in the examples below, compounds of the invention can be co-precipitated with one or more agents such as mannitol, a combination of mannitol and lacto bionic acid, a combination of mannitol and gluconic acid, a combination of mannitol and methanesulfonic acid, a combination of microcrystalline cellulose and oleic acid or a combination of pregelatinized starch and oleic acid. The foregoing examples of one or more agents to aid in preparing formulations of inventive compound are merely illustrative and non-limiting.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. In non-limiting examples, one or more compounds of the invention may be formulated with at least one cytokine, growth factor or other biological, such as an interferon, e.g., alpha interferon, or with at least another small molecule compound. Other non-limiting examples include chemotherapeutic and other anti-cancer agents.

In certain embodiments, the pharmaceutical compositions of the present invention further comprise one or more additional therapeutically active ingredients (e.g., chemotherapeutic, anti-inflammatory and/or palliative). For purposes of the invention, the term "Palliative" refers to treatment that is focused on the relief of symptoms of a disease and/or side effects of a therapeutic regimen, but is not curative. For example, palliative treatment encompasses painkillers, antinausea medications and anti-sickness drugs.

Various embodiments of dosage ranges are contemplated by this invention. In one embodiment the dose amount is based on a weight of peptide per dose. In another embodiment the dose amount is based on a weight of peptide per kilogram of body weight of the patient. The dose amount may be administered daily, twice a day, three times a day, four times a day, or more or less often. The abbreviation mg means milligram and the abbreviation mcg means microgram.

In one embodiment, the dosage is 10-20 mcg per dose. In another embodiment, the dosage is 20-30 mg per dose. In another embodiment, the dosage is 20-40 mcg per dose. In another embodiment, the dosage is 30-60 mcg per dose. In another embodiment, the dosage is 40-80 mcg per dose. In another embodiment, the dosage is 50-100 mcg per dose. In another embodiment, the dosage is 50-150 mcg per dose. In another embodiment, the dosage is 100-200 mcg per dose. In another embodiment, the dosage is 200-300 mcg per dose. In another embodiment, the dosage is 300-400 mcg per dose. In another embodiment, the dosage is 400-600 mcg per dose. In another embodiment, the dosage is 500-800 mcg per dose. In another embodiment, the dosage is 800-1000 mcg per dose.

In one embodiment, the dosage is 10-20 mg per dose. In another embodiment, the dosage is 20-30 mg per dose. In another embodiment, the dosage is 20-40 mg per dose. In another embodiment, the dosage is 30-60 mg per dose. In another embodiment, the dosage is 40-80 mg per dose. In another embodiment, the dosage is 50-100 mg per dose. In another embodiment, the dosage is 50-150 mg per dose. In another embodiment, the dosage is 100-200 mg per dose. In another embodiment, the dosage is 200-300 mg per dose. In another embodiment, the dosage is 300-400 mg per dose. In another embodiment, the dosage is 400-600 mg per dose. In another embodiment, the dosage is 500-800 mg per dose. In another embodiment, the dosage is 800-1000 mg per dose.

In one embodiment, the dosage is 10-20 mcg/kg per dose. In another embodiment, the dosage is 20-30 mcg/kg per dose. In another embodiment, the dosage is 20-40 mcg/kg per dose. In another embodiment, the dosage is 30-60 mcg/kg per dose. In another embodiment, the dosage is 40-80 mcg/kg per dose. In another embodiment, the dosage is 50-100 mcg/kg per dose. In another embodiment, the dosage is 50-150 mcg/kg per dose. In another embodiment, the dosage is 100-200 mcg/kg per dose. In another embodiment, the dosage is 200-300 mcg/kg per dose. In another embodiment, the dosage is 300-400 mcg/kg per dose. In another embodiment, the dosage is 400-600 mcg/kg per dose. In another embodiment, the dosage is 500-800 mcg/kg per dose. In another embodiment, the dosage is 800-1000 mcg/kg per dose.

In one embodiment, the dosage is 10-20 mg/kg per dose. In another embodiment, the dosage is 20-30 mg/kg per dose. In another embodiment, the dosage is 20-40 mg/kg per dose. In another embodiment, the dosage is 30-60 mg/kg per dose. In another embodiment, the dosage is 40-80 mg/kg per dose. In another embodiment, the dosage is 50-100 mg/kg per dose. In another embodiment, the dosage is 50-150 mg/kg per dose. In another embodiment, the dosage is 100-200 mg/kg per dose. In another embodiment, the dosage is 200-300 mg/kg per dose. In another embodiment, the dosage is 300-400 mg/kg per dose. In another embodiment, the dosage is 400-600 mg/kg per dose. In another embodiment, the dosage is 500-800 mg/kg per dose. In another embodiment, the dosage is 800-1000 mg/kg per dose.

In another embodiment, the total amount of peptide per dose or per day is one of the above amounts. In another embodiment, the total peptide dose per dose is one of the above amounts.

Each of the above doses represents a separate embodiment of the present invention.

Methods of Treatment

The single chain peptides embodied here are useful for the treatment of cancer and other dysproliferative diseases. In one embodiment the cancer is a hematopoietic cancer. In other embodiments, the cancer is, by way of non-limiting example, T-cell acute lymphoblastic leukemia or acute lymphocytic leukemia (ALL), acute myeloid leukemia (AML), and chronic myeloid leukemia (CML). Other cancers amenable to the compounds, compositions and uses here include but are not limited to small cell lung cancer, renal cell carcinoma, adenoid cystic carcinoma, squamous cell carcinoma of the head and neck, neuroblastoma and pancreatic cancer. In another embodiment, any cancer in which the interaction of MYB and CBP is pathogenetic is amenable to treatment using the compounds, compositions and methods described herein.

In one embodiment the subject has cancer. In one embodiment, the subject is at risk for developing cancer. In one embodiment, the subject is in remission from cancer. In other embodiments, the cancer is transformed follicular lymphoma, mantel cell lymphoma, breast cancer, ovarian cancer, hepatocellular carcinoma, and non-small cell lung cancer, as well as gastric cancer, Ewing sarcoma and lung adenocarcinoma. These are merely examples of cancers amenable to the methods and uses of the agents herein described.

In another embodiment, the cancer is a lymphoma. In another embodiment, the cancer is a desmoplastic small round cell tumor. In another embodiment, the cancer is a mesothelioma. In another embodiment, the cancer is a gastric cancer. In another embodiment, the cancer is a colon cancer. In another embodiment, the cancer is a lung cancer. In another embodiment, the cancer is a breast cancer. In another embodiment, the cancer is a germ cell tumor. In another embodiment, the cancer is an ovarian cancer. In another embodiment, the cancer is a uterine cancer. In another embodiment, the cancer is a thyroid cancer. In another embodiment, the cancer is a hepatocellular carcinoma. In another embodiment, the cancer is a thyroid cancer. In another embodiment, the cancer is a liver cancer. In another embodiment, the cancer is a renal cancer. In another embodiment, the cancer is a Kaposi's sarcoma. In another embodiment, the cancer is a sarcoma. In another embodiment, the cancer is any other carcinoma or sarcoma.

In another embodiment, the cancer is a solid tumor. In another embodiment, the solid tumor is associated with a cancer. In another embodiment, the solid tumor is associated with a myelodysplastic syndrome (MDS). In another embodiment, the solid tumor is associated with a non-small cell lung cancer (NSCLC). In another embodiment, the solid tumor is associated with a lung cancer. In another embodiment, the solid tumor is associated with a breast cancer. In another embodiment, the solid tumor is associated with a colorectal cancer. In another embodiment, the solid tumor is associated with a prostate cancer. In another embodiment, the solid tumor is associated with an ovarian cancer. In another embodiment, the solid tumor is associated with a renal cancer. In another embodiment, the solid tumor is associated with a pancreatic cancer. In another embodiment, the solid tumor is associated with a brain cancer. In another embodiment, the solid tumor is associated with a gastrointestinal cancer. In another embodiment, the solid tumor is associated with a skin cancer. In another embodiment, the solid tumor is associated with a melanoma.

Methods of Making Peptides

Methods for synthesizing peptides are well known in the art. In another embodiment, the peptides of this invention are synthesized using an appropriate solid-state synthetic procedure (see for example, Steward and Young, Solid Phase Peptide Synthesis, Freemantle, San Francisco, Calif. (1968); Merrifield (1967) Recent Progress in Hormone Res 23: 451). The activity of these peptides is tested, in other embodiments, using assays as described herein.

In another embodiment, the peptides of this invention are purified by standard methods including chromatography (e.g., ion exchange, affinity, and sizing column chromatography), centrifugation, differential solubility, or by any other standard technique for protein purification. In another embodiment, immuno-affinity chromatography is used, whereby an epitope is isolated by binding it to an affinity column comprising antibodies that were raised against that peptide, or a related peptide of the invention, and were affixed to a stationary support.

Materials and Methods.

Cell culture. The human AML lines MV411, MOLM13, ML2, and HL60 were obtained from the American Type Culture Collection (ATCC, Manassas, Va., USA). Umbilical cord blood was obtained from the New York Blood Center. The identity of all cell lines was verified by STR analysis (Genetica DNA Laboratories, Burlington, N.C., USA) and absence of *Mycoplasma* sp. contamination was determined using Lonza MycoAlert (Lonza Walkersville, Inc., Walkersville, Md., USA). Cell lines were cultured in 5% CO2 in a humidified atmosphere at 37° C. in RPMI medium supplemented with 10% fetal bovine serum (FBS) and antibiotics (100 U/ml penicillin and 100 μg/ml streptomycin).

Molecular mechanics simulations. The solution NMR structure of KIX domain of CBP bound to the transactivation domain of C-MYB (PDB code 1SB0) was used as a starting point for simulations of both L- and D-amino acid MYB-CBP complexes. Specifically, the NMR structure with the lowest root-mean-square-deviation (RMSD) from the average of the ensemble of 20 solution NMR structures was selected (model 5). D-amino acid MYB peptide was built with Simulaid program using the NMR structure of protein-peptide complex and converting C-MYB peptide from L-amino acids to D-amino acids in the presence of CBP. Simulations were performed using the Desmond molecular dynamics program. The starting structures were solvated with 6615 and 6714 SPC water molecules, respectively, with a 5 Å buffer of water in a rectangular box. Three chloride ions were added to both systems to maintain electric neutrality. The OPLS3 force field was used to describe both L- and D-amino acid peptide-protein complexes. For each system a relaxation phase, with a combination of Brownian dynamics and restrained molecular dynamics phases was performed to equilibrate the systems. Periodic boundary conditions with a cutoff of 0.9 nm for both particle mesh Ewald and Lennard-Jones interactions were used. Each equilibrated system was then subjected to 60 ns simulations with identical parameters. Simulations were performed using the constant pressure and constant temperature (NPT) ensemble with a Berendsen thermostat and barostat. The equations of motion were integrated using RESPA with a time step of 2.0 fs for bonded and short-range non-bonded interactions, and 6.0 fs for long-range electrostatic interactions. System coordinates were saved every 5 ps.

Expression and purification of recombinant CBP KIX domain. BL21(DE3) cells (Invitrogen) transformed with pGEX-KIX plasmid were induced at 37° C. with isopropyl β-D-1-thiogalactopyranoside for 3 hours. Cells were lysed in 50 mM Tris-HCl pH 7.3, 150 mM NaCl, 0.1% TWEEN-20, 1 mM DTT, 5 mM EDTA, supplemented with protease inhibitors described above and sonicated for ten minutes (15 sec on, 15 sec off, 40% amplitude) using the Misonix probe sonicator (Qsonica, Newtown, Conn.). Lysate was cleared by centrifugation for 1 h at 21,800×g at 4° C. Cleared lysate was incubated with 4 mL glutathione agarose resin slurry (GoldBio) for 1 h at 4° C. to capture GST-KIX. Resin was washed four times with 50 mM Tris-HCl pH 7.4, 150 mM NaCl. KIX domain was cleaved from GST by incubation of resin-bound GST-KIX with 160 U thrombin (GE Healthcare) overnight at room temperature. Resin was centrifuged at 500×g for 5 min. Supernatant containing cleaved KIX was collected and dialyzed at 4° C. against 50 mM MOPS pH 6.5, 50 mM NaCl, 10% glycerol, 1 μM tris-2-carboxyethylphosphine. KIX was purified using a linear gradient of 50 mM to 1 M NaCl by cation exchange chromatography using MonoS 5/50 GL column (GE Healthcare). Fractions containing purified KIX were dialyzed against 50 mM potassium phosphate pH 5.5, 150 mM NaCl, 10 μM tris-2-carboxyethylphosphine, 30% glycerol, and stored at −80° C.

Microscale thermophoresis (MST). For binding affinity studies, interaction of purified recombinant KIX with FITC-conjugated peptides was optimized and performed in MST buffer (50 mM Phosphate, 150 mM NaCl, 0.01% NP-40, pH 5.5) using varying laser powers (FITC-MYB, 250 nM at LED power 40%, FITC-MYBMIM at 500 nM at LED power 50% and FITC-TAT at 500 nM at LED power of 50%) and a blue laser equipped Monolith NT.115 (NanoTemper Technologies). Prior to each run, protein aggregation was minimized by centrifuging the solutions at 15,000 rpm for 8 minutes. FITC-peptide (fixed concentration) was mixed with increasing concentrations of KIX (0.015 to 50 μM) and loaded onto 16 Premium Coated capillaries. The MST measurements were taken at RT and a fixed IR-laser power of 80% for 10 sec per capillary. GraphPad Prism was used to fit the normalized data and determine apparent KD values, represented as percent of fraction bound.

Confocal microscopy. Live confocal imaging was performed using the Leica SP8 confocal microscope and 63× objective with 1 μm z-stack images. Cells were applied to a poly-L-lysine coated chambered Nunc Lab-tek II slide and incubated for 2 hours at 37° C. Prior to imaging, FITC-conjugated peptides were added to cell suspensions at a concentration of 50 nM. Cells were counter-stained using Hoechst 33342 and Mitotracker Red CMX ROS (MProbes) for 10 minutes at a final dilution of 1:10,000 prior to imaging.

Western blot analysis. Cells were lysed in RIPA buffer (Thermo Fisher) supplemented with a protease inhibitor mix comprised of AEBSF (0.5 mM concentration, Santa Cruz, SC-202041B), Bestatin (0.01 mM concentration, Fisher/Alfa Aesar, J61106-MD), Leupeptin (0.1 mM concentration, Santa Cruz, SC-295358B), and Pepstatin (0.001 mM concentration, Santa Cruz, SC-45036A). Lysates were mechanically disrupted using Covaris S220 adaptive focused sonicator, according to the manufacturer's instructions (Covaris, Woburn, Calif.). Lysates were cleared by centrifugation for 15 min at 18,000×g and clarified lysates were quantified using the bicinchoninic acid assay (Pierce). Clarified lysates (20 μg of protein) were resolved using sodium dodecyl sulfate-polyacrylamide gel electrophoresis, and electroeluted using the Immobilon FL PVDF membranes (Millipore, Billerica, Mass., USA). Membranes were blocked using the Odyssey Blocking buffer (Li-Cor, Lincoln, Nebr., USA). The following primary antibodies were used as indicated: anti-MYB (1:500, C-19, Santa Cruz), anti-CBP (1:500, A-22, Santa Cruz), anti-β actin (1:1000, 8H10D10, Cell Signaling). Blotted membranes were visualized using secondary antibodies conjugated to IRDye 800CW or IRDye 680RD (Goat anti-rabbit, 1:15,000, and goat anti-mouse, 1:15,000) and the Odyssey CLx fluorescence scanner, according to manufacturer's instructions (Li-Cor, Lincoln, Nebr., USA).

Co-immunoprecipitation analysis. 7.5 μg of indicated antibodies were conjugated to 1 mg M-270 Epoxy-coated magnetic beads (Invitrogen) according to manufacturer's instructions. 1×10$^7$ MV411 cells were collected and washed in cold PBS. Washed cell pellets were resuspended in 350 μL cold lysis buffer (50 mM Tris-HCl pH 7.4, 150 mM NaCl, 1 mM EDTA, 1 mM DTT, 0.5% Triton X-100, supplemented with protease inhibitors described above) and incubated on ice for 10 min. Cells were mechanically disrupted using the Covaris S220 adaptive focused sonicator at 50 W peak power, 10% duty cycle, 200 cycles per burst at 4° C. for 300 sec. Lysate was clarified by centrifugation for 15 min at 18,000×g at 4° C. Supernatant (cleared lysate) was diluted in 1.05 mL dilution buffer (50 mM Tris-HCl, 150 mM NaCl, 1 mM EDTA, 1 mM DTT, 10% glycerol, supplemented with protease inhibitors described above for a total volume of 1.4 mL. Diluted lysate was added to 1 mg beads, and immunoprecipitation proceeded for 3 h at 4° C. with rotation. Beads were then washed with lysis buffer twice. Proteins were eluted in 20 μL EB buffer (Invitrogen) for 5 min at room temperature, and eluate was neutralized with 2 μL 1M Tris pH 11. Samples were prepared for Western blot by addition of Laemmli buffer with 50 mM DTT and incubation at 95° C. for 5 min. Presence of MYB and CBP was identified by Western blot as described above.

Streptavidin affinity purification. Streptavidin magnetic beads (Pierce) were washed with TBST twice prior to use. Biotinylated MYBMIM (L-aa or D-aa) was conjugated to 150 µL streptavidin bead slurry (1.5 mg beads, binding capacity 3500 pmol biotinylated fluorescein per mg) by incubation at room temperature for 2 h in 1 mL TBST. Peptide-conjugated beads were washed twice in 1 mL TBST. $1 \times 10^7$ cells were collected and washed in cold PBS. Washed cell pellets were lysed in 350 µL of 50 mM Tris-HCl pH 7.4, 150 mM NaCl, 1 mM EDTA, mM DTT, 1% octyl-β-glucoside, 1% Pluronic F-supplemented with 4-(2-aminoethyl)benzenesulfonyl fluoride hydrochloride, bestatin, leupeptin, and pepstatin and incubated on ice for 10 min. Cells were mechanically disrupted using the Covaris S220 adaptive focused sonicator at 50 W peak power, 10% duty cycle, 200 cycles per burst at 4° C. for 300 sec. Lysate was clarified by centrifugation for 15 min at 18,000×g at 4° C. Supernatant (cleared lysate) was diluted in 1.05 mL dilution buffer (50 mM Tris-HCl, 150 mM NaCl, 1 mM EDTA, 1 mM DTT, 10% glycerol, supplemented with protease inhibitors described above) for a total volume of 1.4 mL. TBST was removed from peptide-conjugated streptavidin bead slurry, and diluted lysate was added to 1.5 mg beads. For competition experiments, 10-, 5-, or 2.5-fold excess non-biotinylated peptide was added to the lysate just prior to addition to streptavidin beads. Pulldown and peptide competition proceeded for 3 h at 4° C. with rotation. Beads were washed twice with lysis buffer. Bound proteins were eluted by adding 40 µL Laemmli buffer with 50 mM DTT and incubated for 5 min at 95° C. Presence of CBP was identified by Western blot as described above.

Chromatin immunoprecipitation and sequencing (ChIP-seq). Briefly, cells were fixed in 1% formalin in phosphate-buffered saline (PBS) for 10 minutes at room temperature. Glycine (125 mM final concentration) and Tris-HCl pH 8 (100 mM final concentration) was added to the cells and cells were washed twice in ice-cold PBS and resuspended in sodium dodecyl sulfate (SDS) lysis buffer (1% SDS, 10 mM EDTA, 50 mM Tris-HCl, pH 8.1). Lysates were sonicated using the Covaris S220 adaptive focused sonicator to obtain 100-500 bp chromatin fragments (Covaris, Woburn, Calif.). Lysates containing sheared chromatin fragments were resuspended in 0.01% SDS, 1.1% Triton-X100, 1.2 mM EDTA, 16.7 mM Tris-HCl, pH 8.1, 167 mM NaCl. Lysates and antibody-coupled beads were incubated over night at 4° C. Precipitates were washed sequentially with Mixed Micelle Wash Buffer (15 ml 5M NaCl-150 mM Final, 10 ml 1M Tris-Cl pH 8.1, 5 ml 0.5M EDTA, pH 8.0, 40 ml 65% w/v sucrose, 1 ml 10% NaN3, 25 ml 20% Triton X-100, 10 ml 10% SDS, Add dH2O to 500 ml), LiCl washing solution (0.5% deoxycholic acid, 1 mM EDTA, 250 mM LiCl, 0.5% NP-40, 10 mM Tris-Cl pH 8.0, 0.2% NaN3) and then TBS buffer (20 mM Tris-Cl pH 7.4, 150 mM NaCl). Elution performed in elution buffer (1% SDS, 0.1 M NaHCO3). ChIP-seq libraries were generated using the NEBNext ChIP-seq library prep kit following the manufacturer's protocol (New England Biolabs, Ipswich, Mass., USA). Libraries were sequenced on the Illumina HiSeq 2500 instruments, with 30 million 2×50 bp paired reads.

| Antibody | Manufacturer | Catalog number | Lot | Dilution |
|---|---|---|---|---|
| H3K27ac | Abcam | 4729 | GR200563-2 | 1:100 |
| H3K4me1 | Abcam | 8895 | GR114265-2 | 1:100 |
| H3K4me3 | Cell Signaling Technologies | 9751 | 7 | 1:100 |
| H3K79me3 | Cell Signaling Technologies | 5427 | 4 | 1:100 |
| H3K36me3 | Abcam | 9050 | GR166781-1 | 1:100 |
| H3K27me3 | Millipore | 07-449 | 2736613 | 1:100 |
| CBP | SantaCruz | sc-369, A-22 | L2815 | 1:10 |
| MYB | Abcam | ab45150 | | 1:200 |

Cell viability analysis. Cells were resuspended and plated at a concentration of 2×105 cells in 200 µL in 96-well tissue culture plates. Media with peptides was replaced every 48 hours. To assess the number of viable cells, cells were resuspended in PBS and 10 µL mixed in a 1:1 ratio with 0.4% Trypan Blue (Thermo Fisher) and counted using a hematocytometer (Hausser Scientific, Horsham, Pa., USA). To assess viability using an ATP-based assay, cell viability was assessed using the CellTiter-Glo Luminescent Viability assay, according to the manufacturer's instructions (Promega). Luminescence was recorded using the Infinite M1000Pro plate reader using integration time of 250 milliseconds (Tecan).

Flow cytometric analysis of Apoptosis. Cells were resuspended to a concentration of 1×106 cells were plated in triplicate in a 12-well tissue culture plate. For assessment of annexin V staining, cells were washed with PBS and then resuspended in PBS with Annexin V-APC (BioLegend) and propidium iodide at a dilution of 1:1000. For intracellular detection of cleaved caspase 3, cells were fixed and permeabilized using the BD Cytofix/Cytoperm Fixation/Permeabilization solution according to the manufacturer's instructions (BD Biosciences. Cells were then stained using the Alexa Fluor 647-conjugated anti-active caspase-3 (BD Biosciences) at a dilution of 1:50. Cells were incubated for 30 minutes room temperature in the dark, washed, and then analyzed using the BD LSRFortessa cell analyzer.

Giemsa staining of cells for Morphology. MOLM13 cells were resuspended to a concentration of 1×106 cells in 1 milliliter of PBS. Using the benchtop Cytospin Centrifuge instrument (ThermoFisher Scientific), 200 uL of the cell suspension was applied white clipped Cytofunnels (ThermoFisher Scientific) to glass microscope slides (2×105 cells/slide). Dip Quick Stain (J-322, Jorgensen Laboratories, Inc) was used for per manufacturer's protocol for the polychromic stain of cells.

Quantitative RT-PCR. RNA was isolated using Trizol reagent according to the manufacturer's instructions (Life Technologies). Complementary DNA was synthesized using the SuperScript III First-Strand Synthesis system according to the manufacturer's instructions (Invitrogen). Quantitative real-time PCR was performed using the KAPA SYBR FAST PCR polymerase with 20 ng template and 200 nM primers, according to the manufacturer's instructions (Kapa Biosystems, Wilmington, Mass., USA). PCR primers are listed below. Ct values were calculated using ROX normalization using the ViiA 7 software (Applied Biosystems).

| Primer | Sequence, 5'>3' |
|---|---|
| GAPDH, forward | AATCCCATCACCATCTTCCA (SEQ ID NO: 10) |
| GAPDH, reverse | TGGACTCCACGACGTACTCA (SEQ ID NO: 11) |

-continued

| Primer | Sequence, 5'>3' |
|---|---|
| BCL2, forward | CTGCACCTGACGCCCTTCACC (SEQ ID NO: 12) |
| BCL2, reverse | CACATGACCCCACCGAACTCAAAGA (SEQ ID NO: 13) |
| MYC, forward | TTCCCCTACCCTCTCAACGACAG (SEQ ID NO: 14) |
| MYC, reverse | CCTCATCTTCTTGTTCCTCCTCAG (SEQ ID NO: 15) |

Retrovirus production and cell transduction. The MIG-BCL2 vector was packaged using pUMVc and pCMV-VSVG vectors in HEK 293T cells and the FuGENE 6 transfection reagent, according to manufacturer's instructions (Promega). Virus supernatant was collected at 48 and 72 hours post-transfection, pooled, filtered and stored at −80° C. Cells were transduced with virus particles at a multiplicity of infection of 1 by spin inoculation for 90 minutes at 3500 rpm at 35° C. in the presence of 8 μg/ml hexadimethrine bromide. Two days after transduction, cells were isolated using fluorescence-activated cell sorting (FACSAria III, BD Bioscience, San Jose, Calif., USA).

Blood progenitor colony forming assays. Mononuclear cells were isolated from cord blood using Ficoll-Paque PLUS density centrifugation and enriched for CD34+ cells using the CD34 MicroBead Kit UltraPure, according to the manufacturer's instructions (Miltenyi Biotech). CD34+ cells were resuspended to a concentration of 1×105 cells/mL. Methocult H4303 Optimum (Stemcell Technologies, Catalog no. 04034 with FBS, BSA and recombinant cytokines rhSCF, rhGM-CSF, rhG-CSF, rhIL3, and rhErythropoietin) semi-solid media was used for the growth of hematopoietic progenitor cells in colony-forming units. Methocult and CD34+ cells were mixed in a ratio of 1:10 (cells:Methocult) for a final cell concentration plated of 1000 cells/dish. TG3 or MYBMIM peptide were added to this solution for a final concentration of 20 □M. Mixture was vortexed for 30 seconds and incubated at room temperature for 5 minutes. Using a blunt end 18G needle, 1.1 mL of the solution was added to a 35×10 mm dish and then tilted to provide even coverage on plate. Peptide treatment conditions were plated in biological triplicates. 35×10 mm dishes placed into a larger 100×15 mm dish with 1 35×10 mm dish filled with sterile H20). Dishes were incubated at 37° C. with 5% CO2 for 14 days. Both erythroid progenitor and granulocyte-macrophage progenitors were observed and quantified.

Mouse studies. All mouse experiments were carried out in accordance with institutional animal protocols. Two hundred thousand primary AML MLL-rearranged leukemia cells were suspended in 200 ml of PBS and transplanted via tail vein injection into 8-week-old sublethally irradiation (200 rad) female NOD.Cg-Prkdc(scid)Il2rg(tm1Wjl)/SzJ mice (The Jackson Laboratory, Bar Harbor, Me., USA). Recipient mice were maintained on antibiotic supplementation in chow (0.025% trimethoprim, 0.124% sulfamethoxazole, Sulfatrim). Three days after transplant, mice were randomly assigned to experimental treatment groups. MYBMIM peptide suspended in PBS was administered daily through intraperitoneal injection at a daily dose of 50 mg/kg. Mice were treated from days 3-17 of this study for a total of 14 days and then monitored daily with clinical examination for survival analysis.

Statistical Analysis. For comparisons between two sample sets, statistical analysis of means was performed using 2-tailed, unpaired Student's t-tests. Survival analysis was done using the Kaplan-Meier method, as assessed using a log-rank test. For gene expression analysis, statistical significance was assessed using paired t-tests.

Example 1. Peptide Competes with the MYB:CBP Complex in AML

Figure 1B:
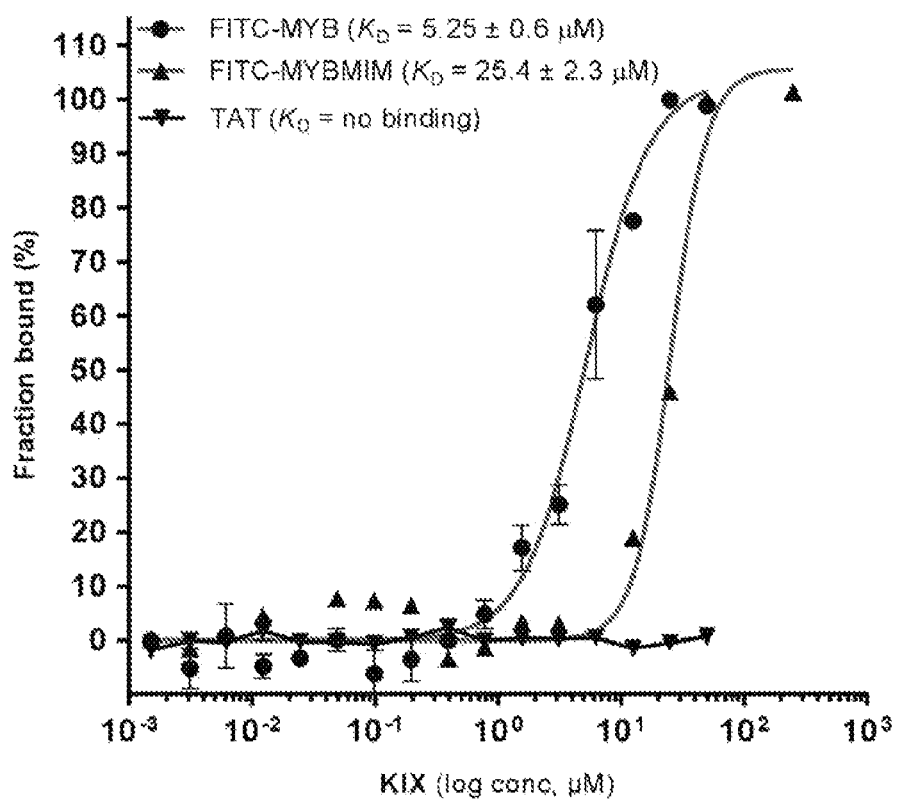
Figure 1C:
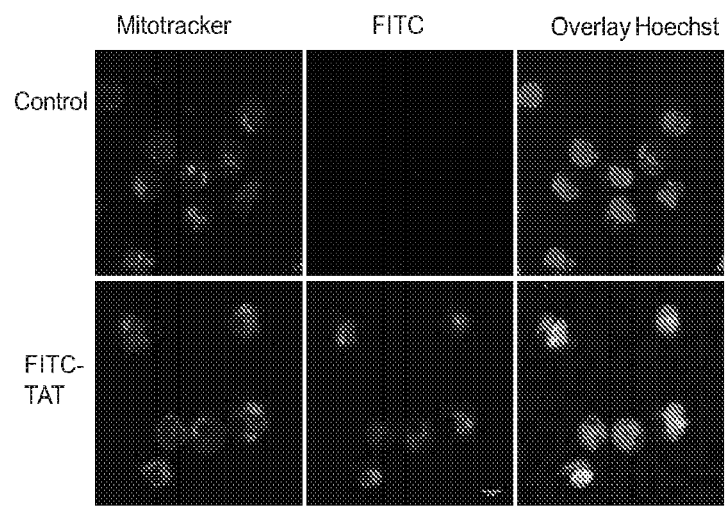
Figure 1D:
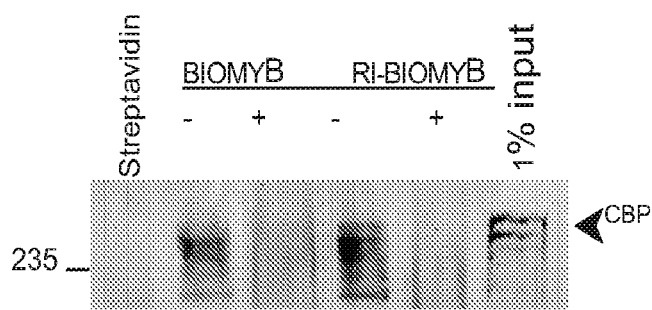

Through molecular modeling, there is in vitro binding of engineered L-amino acid (L-aa; SEQ ID NO:2) and D-amino acid (Daa; SEQ ID NO:1) containing peptides to CBP (FIG. 1a). Both Laa and Daa peptides were conjugated to FITC by the Tufts University Core Facility. Through plasmid DNA isolation from a pGEX backbone, the KIX domain of CBP was purified and utilized to determine binding affinity to both FITC-conjugated peptides. Using the NanoTemper NT115 instrument, binding affinity was established in a microscale thermopheresis binding assay (FIG. 1b). The rapid and efficient intracellular penetration of a FITC-conjugated peptide (SEQ ID NO:6) in a human AML cell line using confocal microscopy was demonstrated. There is intranuclear penetration of the FITC-conjugated peptide after incubation with 50 nM concentration of peptide for 20 minutes indicated by the FITC-Hoechst overlay (FIG. 1c). In a biochemical pull-down assay, using biotinylated MYBMIM (SEQ ID NO:5), streptavidin coated beads were treated with BIOMYB (SEQ ID NO:4) and with AML cell lysates and were able to pull down CBP. This shows that there is specific binding of the MYBMIM peptide (SEQ ID NO:1) to its target CBP (FIG. 1d). In showing the binding and intracellular penetration of these peptides, biochemical assays here support that MYBMIM (SEQ ID NO:1) is competing in a specific manner with the MYB:CBP complex in AML cells.

Detailed description of FIG. 1: MYBMIM competes with the MYB:CBP complex in AML. (a) Molecular Dynamic Simulation modeling was performed to compare the molecular interactions within the native MYB:CBP complex to the interaction between a MYB peptide to CBP (L-amino acid peptide, labeled as L-aa (SEQ ID NO:2), and D-amino acid, labeled MYBMIM, SEQ ID NO:1, are compared here). There was no significant difference in the conformation of MYB:CBP complex structures. (b) Microscale Thermopheresis (MST) was performed here to analyze the binding affinity of MYB peptides to the purified CBP-KIX domain. FITC-MYB (L-aa peptide, green line, KD=5.25+0.6 μM) interacts with purified KIX at a higher binding affinity than FITC-MYBMIM (D-aa peptide, red line, KD=25.4+2.3 μM). There is no interaction seen between FITC-TAT and KIX (black line), n=3 for each curve. (c) The intranuclear penetration of FITC-labelled TAT peptides in MOLM13 cells is shown here using confocal microscopy. In FITC-TAT treated cells, there is an overlap of FITC and Hoechst in the nucleus as compared to control, untreated, cells. One micron z-stack images were obtained using a 63× objective and 2× zoom with a single stack image of maximum projection shown here (scale bar indicates 10 microns). (d) Western blot showing specific binding of biotinylated-MYBMIM to CBP in MV411 human AML cells. BIOMYB indicates biotinylated MYBMIM containing L-aa and RI-BIOMYB (SEQ ID NO:5) indicates biotinylated MYBMIM containing D-aa. + or − symbols indicate the presence or absence of respective non-biotinylated peptide, showing specific competition of CBP binding in cells.

Example 2. Peptide Downregulates MYB-Regulated Genes and Induces Apoptosis

Figure 2A:
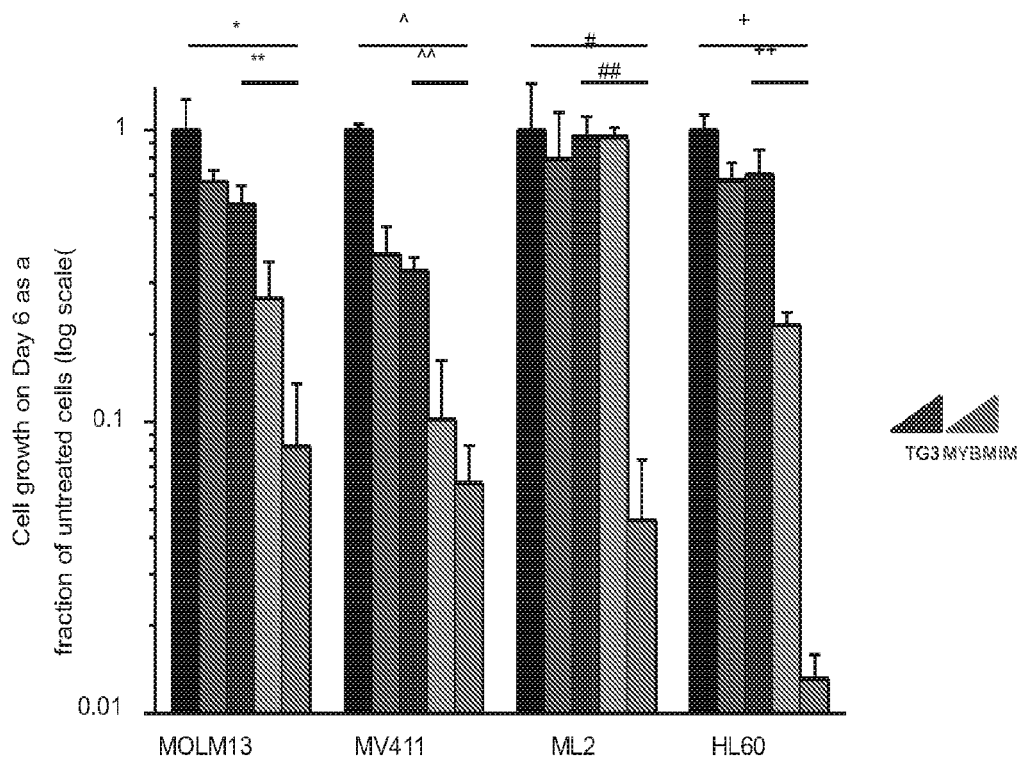
FIG. 2a-g show that a compound of the invention down-regulates MYB-regulated genes and induces apoptosis.
Figure 2B:
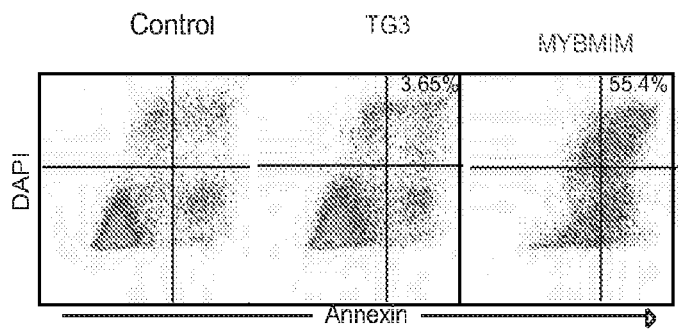
Figure 2C:
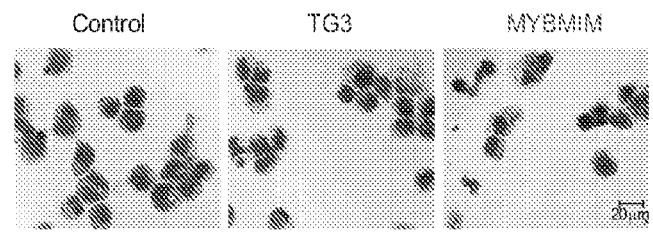
Figure 2D:
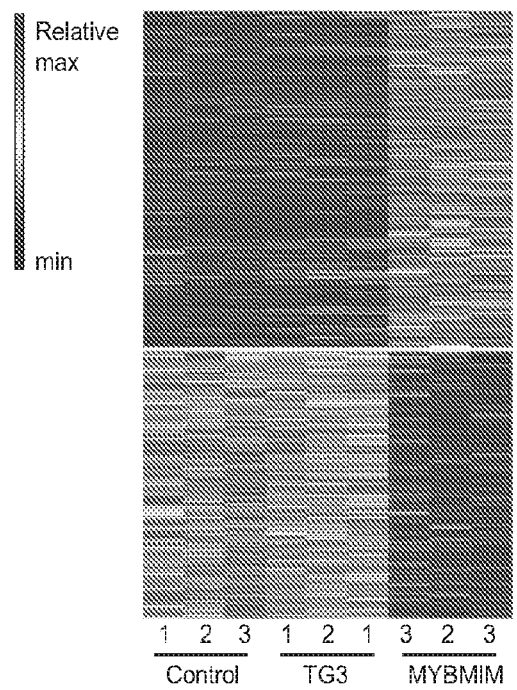
Figure 2E:
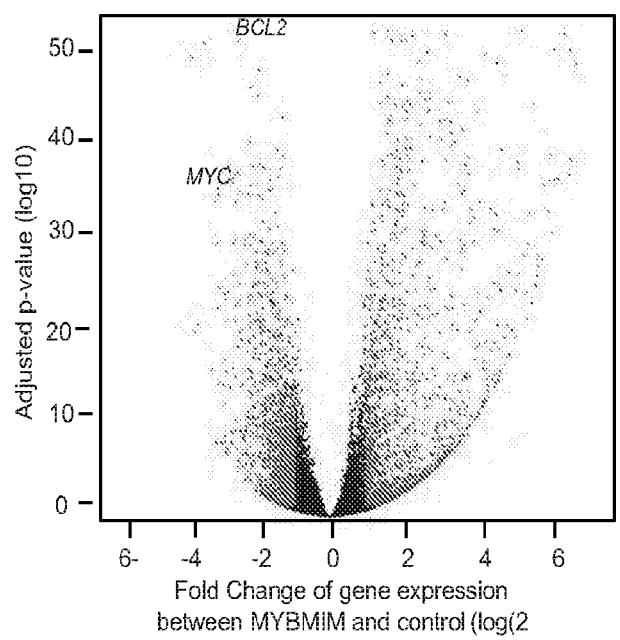
Figure 2F:
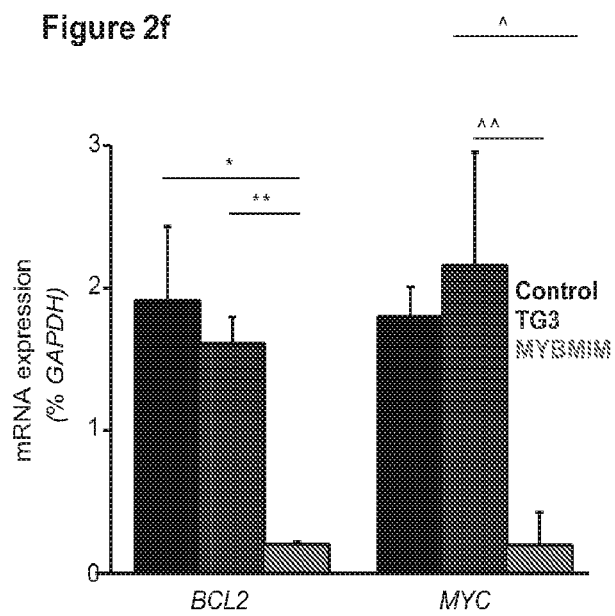
Figure 2G:
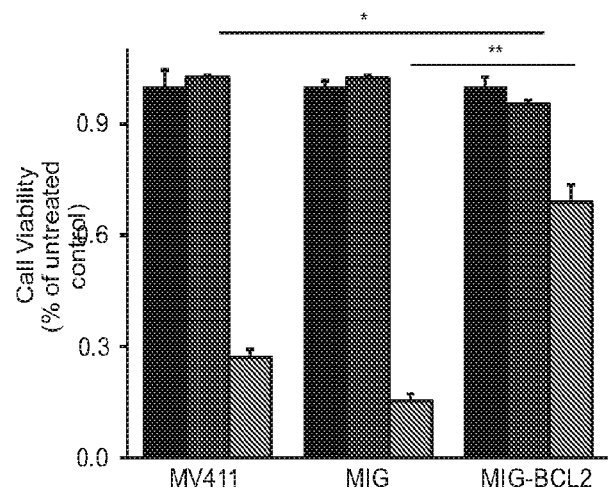
Figure 3A:
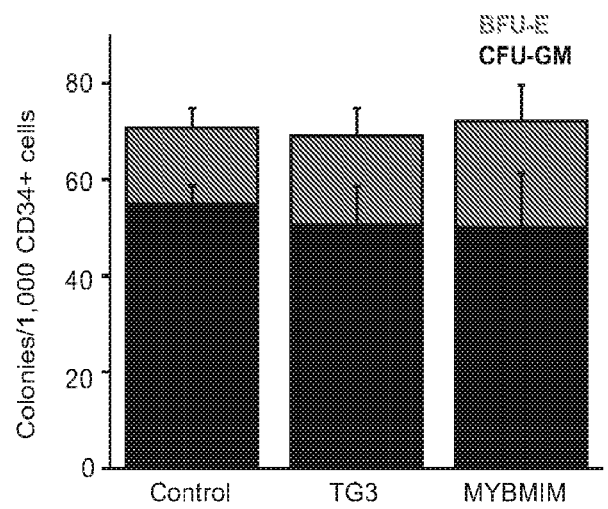
FIGS. 3a-d show that a compound of the invention exhibits anti-leukemia efficacy in vivo
Figure 3B:
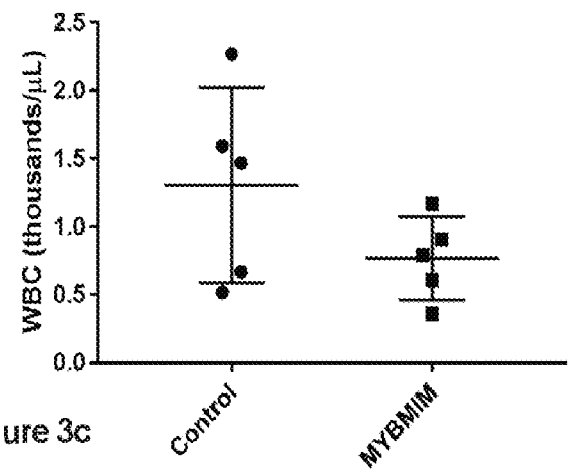
Figure 3C:
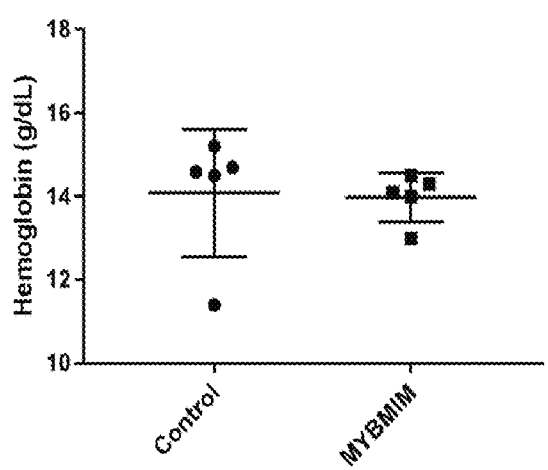
Figure 3D:
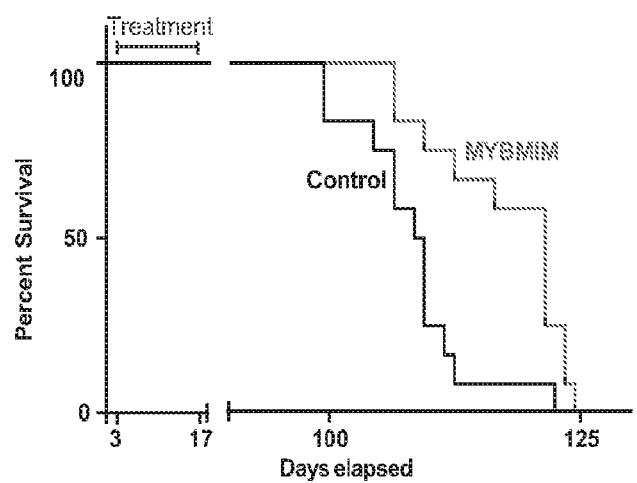

Treatment of human AML cell lines with MYBMIM in vitro reveals an induction of AML cell death that is seen in MOLM13, MV411, ML2, and HL60 cell lines in a dose-dependent effect with MYBMIM, 10 μM and 20 μM doses, as compared to its inactive isostere TG3, 10 μM and 20 μM doses (FIG. 2a). Flow cytometric analysis of apoptosis using Annexin-V APC staining in MV411 cells in vitro with MYBMIM treatment at 20 μM dose for 24 hours (FIG. 2b) reveals an induction of apoptosis. Morphological changes are evident in Wright-Giemsa stains of cytospun MV411 cells with cell death seen at 40× immersion oil microscopy (FIG. 2c). In trying to identify the downstream gene expression effects of MYBMIM in human AML cells, human AML cells were treated for six hours with the MYBMIM peptide, using both TG3 inactive peptide and control untreated cells as negative controls. RNA-seq data reveals significant down-regulation of MYB-dependent gene expression in MYBMIM treatment vs TG3 and control (FIGS. 2d) and a volcano plot (FIG. 2e) comparing the log-fold change vs p-adjusted values reveals significantly downregulated genes BCL2 and MYC, which are highlighted. To confirm this pattern of MYB-dependent downregulation, RT-qPCR was performed to show downregulation of MYC and BCL2 mRNA expression in human AML cell lines as a percentage of GAPDH, (FIG. 2f). Ectopic expression of Bcl2 in MV411 cells reveals a partial rescue of the MYBMIM induced apoptosis as measured in a cell viability assay using the CellTiter Glo reagent kit, (FIG. 2g). There is reproducible downregulation of MYB target genes with a specific effect of AML cell death that is mediated through apoptosis.

Detailed description of FIG. 2: MYBMIM downregulates MYB-regulated genes and induces apoptosis. (a) Quantification of live AML cells using Trypan blue exclusion after MYBMIM treatment. Live MOLM13, MV411, ML2, and HL60 cells were counted on Day 6 using a hemocytometer. Peptide treatment was applied directly to cell culture with inactive TG3 (dosed at 10 μM and 20 μM) and MYBMIM (dosed at 10 μM and 20 μM) every 48 hours for a 6 day period. Cells were plated and treated in biological triplicates with symbols indicating $p<0.05$ (*$p=0.0046$, **$p=0.0011$, ^$p=0.00001$, ^^$p=0.0004$, #$p=0.05$, ##$p=0.0039$, +$p=0.00016$, ++$p=0.0013$). Each set of bars represents, from left to right, control, TG3 at 10 μM, TG3 at 20 μM, MYBMIM at 10 μM, MYBMIM at 20 μM. (b) Induction of apoptosis observed with MYBMIM treatment of human AML cells. Flow cytometric analysis of Annexin-V and DAPI staining of MOLM13 cells after treatment with TG3 (20 μM) and MYBMIM (20 μM) for 24 hours. % indicating percentage of cells that are both Annexin and DAPI positive. (c) MYBMIM induces cell death without morphologic evidence of differentiation. Representative Giemsa stained images of MOLM13 cells after treatment with TG3 (20 μM) and MYBMIM (20 μM) for 6 hours. Microscopy performed here with 40× magnification and using immersion oil (scale bar indicates 20 microns). (d) Heatmap showing MYBMIM-induced gene expression changes in MOLM13 cells after 6 hour treatment with TG3 (20 μM) and MYBMIM (20 μM). Heatmap is generated with values and corresponding color index (shown here in gray scale) that are row-normalized. Biological triplicate samples are indicated as 1-3 per sample treatment condition. (e) Volcano plot of MYBMIM treated MV411 human AML cells compared to control. The x-axis is denoted as the Fold change of gene expression between MYBMIM and control (log 2) and the y-axis is the Adjusted p-value (log 10). Representative MYB-dependent genes, MYC and BCL2, are significantly downregulated. (f) BCL2 and MYC mRNA expression was measured by RT-qPCR and normalized to glyceraldehyde-3-phosphate dehydrogenase (GAPDH) expression. Symbols indicate $p<0.05$ (*$p=0.0046$, **$p=0.00023$, ^$p=0.00082$, ^^$p=0.0148$). Each set of bars represent, from left to right, control, TG3 and MYBMIM. (g) Ectopic expression of MSCV-Ires-GFP vector containing BCL2 in MV411 cells partially rescues MYBMIM-induced apoptosis, shown here by measurement of ATP activity using a CellTiter Glo luminescence assay. % Cell viability is calculated as a fraction of untreated control. Symbols indicate (*$p=0.00026$, **$p=0.00005$). Error bars represent standard deviation of the mean of 3 biological replicates. Each set of bars represent, from left to right, control, TG3 and MYBMIM.

Example 3. Peptide Exhibits Anti-Leukemic Efficacy In Vivo

Figure 4A:
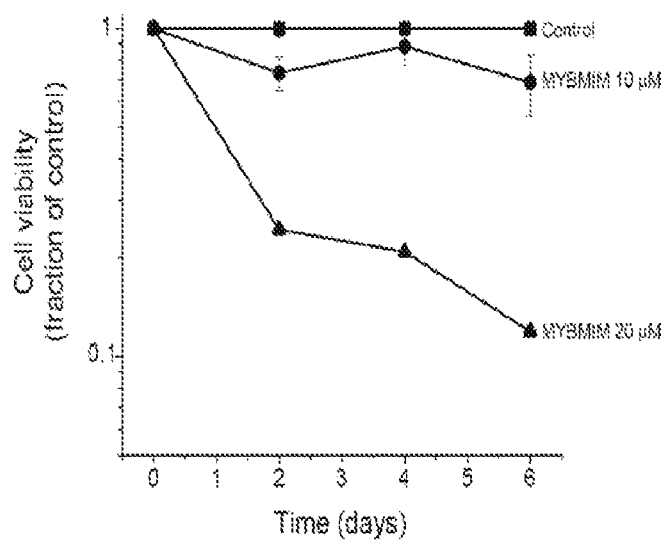
Figure 4B:
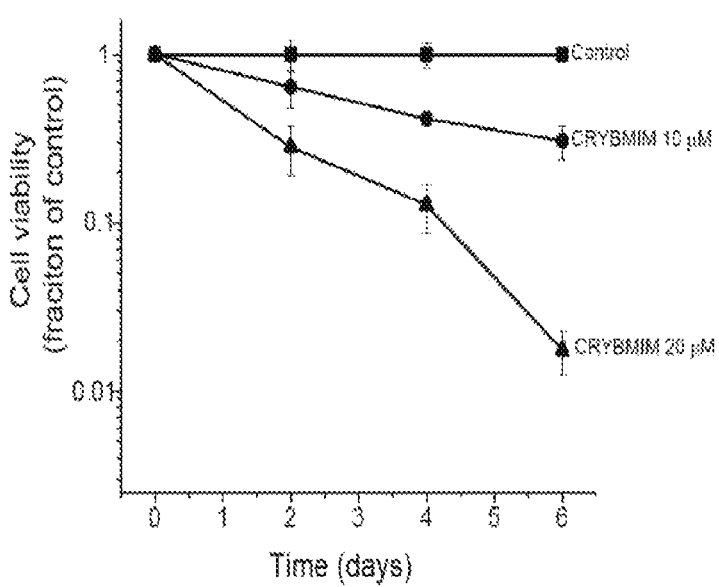

The anti-leukemic therapeutic efficacy of the MYBMIM peptide was investigated using a primary patient derived xenograft model. In this model, $5 \times 10^5$ cells of a primary MLL-rearranged AML were transplanted via tail vein injection into sublethally irradiated NSG mice. In one xenograft model, after peripheral blood engraftment was confirmed (range of 1-7% hCD45), mice were randomized to cohorts (n=15) of either treatment with MYBMIM (25 mg/kg daily) or vehicle, all via intraperitoneal injection for 21 days. At the end of the treatment period, bilateral femurs were harvested, formalin fixed, paraffin embedded, and sectioned for Immunohistochemical staining of hCD45. In this analysis of bone marrows using hCD45 staining, MYBMIM induces a decrease in the leukemia burden in mice. Representative images are shown using 40× magnification (FIG. 4b). In a subsequent xenograft experiment, 5×105 cells of a primary MLL-rearranged AML were transplanted via tail vein injection into sublethally irradiated NSG mice. After a 3-day post-transplant period, mice were randomized to cohorts (n=15) of either treatment with MYBMIM (50 mg/kg daily) or vehicle, all via intraperitoneal injection. The endpoint analysis of this in vivo model was a survival analysis where MYBMIM prolongs survival of mice, Kaplan-Meier survival curve log-rank analysis of $p=0.0038$ (FIG. 4c).

Detailed description of FIG. 3: MYBMIM exhibits anti-leukemia efficacy in vivo. (a) MYBMIM has no significant effect on colony formation of CD34-enriched hematopoietic progenitor cells isolated from human umbilical cord blood and grown in growth-factor enriched semi-solid media. The number of burst forming units-erythroid (BFU-E) and colony forming units-Granulocyte/Monocyte (CFU-GM) and were measured here in control, TG3 and MYBMIM treatment conditions. The bottom section of each bar represents CFU-GM, and the top section BFU-E. A study of MYBMIM toxicity in NSG mice was performed with 25 mg/kg daily intraperitoneal dosing for 7 days. Complete blood count (CBC) analysis was obtained from peripheral blood samples by using a HemaVet950 with no significant differences in MYBMIM treated mice versus vehicle control in both (b) white blood cell counts, WBC, measured in thousands/μL and in (c) hemoglobin, measured in g/dL, n=5 for each treatment group. (d) Survival analysis of primary patient-derived MLL-rearranged leukemia cells (5×10^5 cells per mouse via tail vein injection) engrafted into sublethally irradiated immunodeficient mice and treated with MYBMIM via intraperitoneal injection for 14 days (indicated as Treatment from days 3-17), p=0.0038. Error bars represent standard deviation of the mean of 3 biological replicates.

Example 4. Additional Data on Peptides

Using the methods as described above, the activity of the peptides of SEQ ID NOs:1 and 25 were evaluated in a cell viability assay using AML cell line MV411. Quantification of live AML cells using Trypan blue exclusion after MYB-MIM treatment. Live MV411 cells were counted on days 2, 4, and 6 using a hemocytometer. Peptide treatment was applied directly to cell culture with SEQ ID NO:1 (MYB-MIM; 4a) and SEQ ID NO:25 (CRYBMIM; 4b) (dosed at 10 and 20 µM) every 48 hours for a 6 day period. Cells were plated and treated in biological triplicates. These peptides were tested at 20 µM dose across a panel of AML cell lines and the results from day 6 of treatment are shown in FIG. 4c for SEQ ID NO:1 and in FIG. 4d for SEQ ID NO:25. Each cell line control was set at 1 (black line), and cell viability for each cell line is plotted as a fraction of its respective control.

What is claimed is:

1. A single chain peptide consisting of D-amino acids and comprising: an N-terminal portion comprising the amino acid sequence selected from KLENETSMLLLELEKIRK (SEQ ID NO:19) and KLENETSMLLLEL (SEQ ID NO:24); a C-terminal portion comprising the amino acid sequence RRRQRRKKRGY (SEQ ID NO:17); and the amino acid sequence therebetween selected from PADSSLDNLIKRYpSPRRSLIERR (SEQ ID NO:33), KRYpSPRRSLIERR (SEQ ID NO:23) and PADSSLDNLIKRYpS (SEQ ID NO:34).

2. The single chain peptide of claim 1, wherein a linker is present between the amino acid sequences thereof.

3. The single chain peptide of claim 2, wherein the linker is GG.

4. The single chain peptide of claim 1, wherein the single chain peptide consists of the D-amino acid sequence KLENETSMLLLELKRYpSPRRSLIERRGGRRRQRRKKRGY (SEQ ID NO:25).

5. The single chain peptide of claim 4, wherein the N-terminus is acetylated, the C-terminus is amidated, or the combination thereof.

6. The single chain peptide of claim 1, wherein the N-terminus is acetylated, the C-terminus is amidated, or the combination thereof.

7. The single chain peptide of claim 1, wherein the single chain peptide comprises the D-amino acid sequence KLENETSMLLLELKRYpSPRRSLIERRGGRRRQRRKKRGY (SEQ ID NO:25).

8. The single chain peptide of claim 7, wherein the N-terminus is acetylated, the C-terminus is amidated, or the combination thereof.

9. A method for treating acute myeloid leukemia comprising administering to a patient in need thereof an effective amount of a composition comprising a peptide of claim 1, and a carrier, excipient or diluent.

* * * * *

```
                           SEQUENCE LISTING

<160> NUMBER OF SEQ ID NOS: 39

<210> SEQ ID NO 1
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: Mod_Res
<222> LOCATION: (1)..(31)
<223> OTHER INFORMATION: D-amino acids
<220> FEATURE:
<221> NAME/KEY: Mod_Res
<222> LOCATION: (1)..(1)
<223> OTHER INFORMATION: N-terminal acetyl
<220> FEATURE:
<221> NAME/KEY: Mod_Res
<222> LOCATION: (31)..(31)
<223> OTHER INFORMATION: C-terminal amide

<400> SEQUENCE: 1

Lys Leu Glu Asn Glu Thr Ser Met Leu Leu Leu Glu Leu Glu Lys Ile
1               5                   10                  15

Arg Lys Gly Gly Arg Arg Arg Gln Arg Lys Lys Arg Gly Tyr
            20                  25                  30

<210> SEQ ID NO 2
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: Mod_Res
<222> LOCATION: (1)..(1)
<223> OTHER INFORMATION: N-terminal acetyl
<220> FEATURE:
<221> NAME/KEY: Mod_Res
<222> LOCATION: (31)..(31)
<223> OTHER INFORMATION: C-terminal amide

<400> SEQUENCE: 2

Tyr Gly Arg Lys Lys Arg Arg Gln Arg Arg Arg Gly Gly Lys Arg Ile
1               5                   10                  15

Lys Glu Leu Glu Leu Leu Leu Met Ser Thr Glu Asn Glu Leu Lys
            20                  25                  30

<210> SEQ ID NO 3
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: Mod_Res
```

```
<222> LOCATION: (1)..(31)
<223> OTHER INFORMATION: D-amino acids
<220> FEATURE:
<221> NAME/KEY: Mod_Res
<222> LOCATION: (1)..(1)
<223> OTHER INFORMATION: N-terminal acetyl
<220> FEATURE:
<221> NAME/KEY: Mod_Res
<222> LOCATION: (31)..(31)
<223> OTHER INFORMATION: C-terminal amide

<400> SEQUENCE: 3

Lys Leu Gly Asn Glu Thr Ser Met Gly Leu Leu Glu Leu Glu Lys Ile
1               5                   10                  15

Gly Lys Gly Gly Arg Arg Arg Gln Arg Arg Lys Lys Arg Gly Tyr
            20                  25                  30

<210> SEQ ID NO 4
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: N-terminal biotin
<220> FEATURE:
<221> NAME/KEY: MOD_RES
<222> LOCATION: (31)..(31)
<223> OTHER INFORMATION: C-terminal amide

<400> SEQUENCE: 4

Tyr Gly Arg Lys Lys Arg Arg Gln Arg Arg Gly Gly Lys Arg Ile
1               5                   10                  15

Lys Glu Leu Glu Leu Leu Leu Met Ser Thr Glu Asn Glu Leu Lys
            20                  25                  30

<210> SEQ ID NO 5
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: Mod_res
<222> LOCATION: (1)..(1)
<223> OTHER INFORMATION: N-terminal acetyl
<220> FEATURE:
<221> NAME/KEY: Mod_res
<222> LOCATION: (1)..(32)
<223> OTHER INFORMATION: D-amino acids
<220> FEATURE:
<221> NAME/KEY: Mod_res
<222> LOCATION: (32)..(32)
<223> OTHER INFORMATION: C-terminal biotin-NH2

<400> SEQUENCE: 5

Lys Leu Glu Asn Glu Thr Ser Met Leu Leu Leu Glu Leu Glu Lys Ile
1               5                   10                  15

Arg Lys Gly Gly Arg Arg Arg Gln Arg Arg Lys Lys Arg Gly Tyr Lys
            20                  25                  30

<210> SEQ ID NO 6
<211> LENGTH: 11
<212> TYPE: PRT
<213> ORGANISM: Artificial Sequence
<220> FEATURE:
<223> OTHER INFORMATION: Synthetic
<220> FEATURE:
```

```
<221> NAME/KEY: mod_res
<222> LOCATION: (1)..(1)
<223> OTHER INFORMATION: N-terminal-FITC-AHA
<220> FEATURE:
<221> NAME/KEY: mod_res
<222> LOCATION: (1)..(11)
<223> OTHER INFORMATION: D-amino acids
<220> FEATURE:
<221> NAME/KEY: mod_res
<222> LOCATION: (11)..(11)
<223> OTHER INFORMATION: C-terminal amide

<400> SEQUENCE: 6

Tyr Gly Arg Lys Lys Arg Arg Gln Arg Arg
1               5                   10

<210> SEQ ID NO 7
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: mod_res
<222> LOCATION: (1)..(31)
<223> OTHER INFORMATION: D-amino acids

<400> SEQUENCE: 7

Lys Leu Glu Asn Glu Thr Ser Met Leu Leu Leu Glu Leu Glu Lys Ile
1               5                   10                  15

Arg Lys Gly Gly Arg Arg Arg Gln Arg Arg Lys Lys Arg Gly Tyr
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: Synthetic

<400> SEQUENCE: 8

Tyr Gly Arg Lys Lys Arg Arg Gln Arg Arg Gly Gly Lys Arg Ile
1               5                   10                  15

Lys Glu Leu Glu Leu Leu Leu Met Ser Thr Glu Asn Glu Leu Lys
            20                  25                  30

<210> SEQ ID NO 9
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: mod_res
<222> LOCATION: (1)..(1)
<223> OTHER INFORMATION: N-terminal FITC-AHA
<220> FEATURE:
<221> NAME/KEY: mod_res
<222> LOCATION: (1)..(8)
<223> OTHER INFORMATION: D-amino acids
<220> FEATURE:
<221> NAME/KEY: mod_res
<222> LOCATION: (18)..(18)
<223> OTHER INFORMATION: C-terminal amide

<400> SEQUENCE: 9

Lys Leu Glu Asn Glu Thr Ser Met Leu Leu Leu Glu Leu Glu Lys Ile
1               5                   10                  15

Arg Lys
```

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
aatcccatca ccatcttcca                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
tggactccac gacgtactca                                              20

<210> SEQ ID NO 12
<211> LENGTH: 21
<212> TYPE: DNA
<213> ORGANISM: Artificial Sequence
<220> FEATURE:
<223> OTHER INFORMATION: Synthetic

<400> SEQUENCE: 12
ctgcacctga cgcccttcac c                                            21

<210> SEQ ID NO 13
<211> LENGTH: 25
<212> TYPE: DNA
<213> ORGANISM: Artificial Sequence
<220> FEATURE:
<223> OTHER INFORMATION: Synthetic

<400> SEQUENCE: 13
cacatgaccc caccgaactc aaaga                                        25

<210> SEQ ID NO 14
<211> LENGTH: 23
<212> TYPE: DNA
<213> ORGANISM: Artificial Sequence
<220> FEATURE:
<223> OTHER INFORMATION: Synthetic

<400> SEQUENCE: 14
ttcccctacc ctctcaacga cag                                          23

<210> SEQ ID NO 15
<211> LENGTH: 24
<212> TYPE: DNA
<213> ORGANISM: Artificial Sequence
<220> FEATURE:
<223> OTHER INFORMATION: Synthetic

<400> SEQUENCE: 15
cctcatcttc ttgttcctcc tcag                                         24

<210> SEQ ID NO 16
<211> LENGTH: 10
<212> TYPE: PRT
<213> ORGANISM: Artificial Sequence
<220> FEATURE:

```
<223> OTHER INFORMATION: Synthetic

<400> SEQUENCE: 16

Tyr Gly Arg Lys Lys Arg Arg Gln Arg Arg
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: mod_res
<222> LOCATION: (1)..(11)
<223> OTHER INFORMATION: D-amino acids

<400> SEQUENCE: 17

Arg Arg Arg Gln Arg Arg Lys Lys Arg Gly Tyr
1               5                   10

<210> SEQ ID NO 18
<211> LENGTH: 18
<212> TYPE: PRT
<213> ORGANISM: Artificial Sequence
<220> FEATURE:
<223> OTHER INFORMATION: Synthetic

<400> SEQUENCE: 18

Lys Arg Ile Lys Glu Leu Glu Leu Leu Leu Met Ser Thr Glu Asn Glu
1               5                   10                  15

Leu Lys

<210> SEQ ID NO 19
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: mod_res
<222> LOCATION: (1)..(18)
<223> OTHER INFORMATION: D-amino acids

<400> SEQUENCE: 19

Lys Leu Glu Asn Glu Thr Ser Met Leu Leu Glu Leu Glu Lys Ile
1               5                   10                  15

Arg Lys

<210> SEQ ID NO 20
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: mod_res
<222> LOCATION: (10)..(10)
<223> OTHER INFORMATION: phosphoserine

<400> SEQUENCE: 20

Arg Arg Glu Ile Leu Ser Arg Arg Pro Ser Tyr Arg Lys
1               5                   10

<210> SEQ ID NO 21
<211> LENGTH: 13
<212> TYPE: PRT
```

```
<213> ORGANISM: Artificial Sequence
<220> FEATURE:
<223> OTHER INFORMATION: Synthetic

<400> SEQUENCE: 21

Leu Glu Leu Leu Leu Met Ser Thr Glu Asn Glu Leu Lys
1               5                   10

<210> SEQ ID NO 22
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: mod_res
<222> LOCATION: (23)..(23)
<223> OTHER INFORMATION: phosphoserine

<400> SEQUENCE: 22

Tyr Gly Arg Lys Lys Arg Arg Gln Arg Arg Gly Gly Arg Glu
1               5                   10                  15

Ile Leu Ser Arg Arg Pro Ser Tyr Arg Lys Leu Glu Leu Leu Leu Met
            20                  25                  30

Ser Thr Glu Asn Glu Leu Lys
        35

<210> SEQ ID NO 23
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: mod_res
<222> LOCATION: (1)..(13)
<223> OTHER INFORMATION: D-amino acids
<220> FEATURE:
<221> NAME/KEY: mod_res
<222> LOCATION: (4)..(4)
<223> OTHER INFORMATION: phosphoserine

<400> SEQUENCE: 23

Lys Arg Tyr Ser Pro Arg Arg Ser Leu Ile Glu Arg Arg
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: mod_res
<222> LOCATION: (1)..(13)
<223> OTHER INFORMATION: D-amino acids

<400> SEQUENCE: 24

Lys Leu Glu Asn Glu Thr Ser Met Leu Leu Leu Glu Leu
1               5                   10

<210> SEQ ID NO 25
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: mod_res
```

```
<222> LOCATION: (1)..(39)
<223> OTHER INFORMATION: D-amino acids
<220> FEATURE:
<221> NAME/KEY: mod_res
<222> LOCATION: (17)..(17)
<223> OTHER INFORMATION: phosphoserine

<400> SEQUENCE: 25

Lys Leu Glu Asn Glu Thr Ser Met Leu Leu Leu Glu Leu Lys Arg Tyr
1               5                   10                  15

Ser Pro Arg Arg Ser Leu Ile Glu Arg Arg Gly Gly Arg Arg Arg Gln
            20                  25                  30

Arg Arg Lys Lys Arg Gly Tyr
        35

<210> SEQ ID NO 26
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: mod_res
<222> LOCATION: (1)..(1)
<223> OTHER INFORMATION: N-terminal acetyl
<220> FEATURE:
<221> NAME/KEY: mod_res
<222> LOCATION: (23)..(23)
<223> OTHER INFORMATION: phosphoserine
<220> FEATURE:
<221> NAME/KEY: mod_res
<222> LOCATION: (39)..(39)
<223> OTHER INFORMATION: C-terminal amide

<400> SEQUENCE: 26

Tyr Gly Arg Lys Lys Arg Arg Gln Arg Arg Gly Gly Arg Arg Arg Glu
1               5                   10                  15

Ile Leu Ser Arg Arg Pro Ser Tyr Arg Lys Leu Glu Leu Leu Leu Met
            20                  25                  30

Ser Thr Glu Asn Glu Leu Lys
        35

<210> SEQ ID NO 27
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: mod_res
<222> LOCATION: (1)..(1)
<223> OTHER INFORMATION: N-terminal acetyl
<220> FEATURE:
<221> NAME/KEY: mod_res
<222> LOCATION: (17)..(17)
<223> OTHER INFORMATION: phosphoserine
<220> FEATURE:
<221> NAME/KEY: mod_res
<222> LOCATION: (39)..(39)
<223> OTHER INFORMATION: C-terminal amide

<400> SEQUENCE: 27

Lys Leu Glu Asn Glu Thr Ser Met Leu Leu Leu Glu Leu Lys Arg Tyr
1               5                   10                  15

Ser Pro Arg Arg Ser Leu Ile Glu Arg Arg Gly Gly Arg Arg Arg Gln
            20                  25                  30

Arg Arg Lys Lys Arg Gly Tyr
        35
```

```
<210> SEQ ID NO 28

<400> SEQUENCE: 28

000

<210> SEQ ID NO 29
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: mod_res
<222> LOCATION: (10)..(10)
<223> OTHER INFORMATION: phosphoserine

<400> SEQUENCE: 29

Arg Arg Glu Ile Leu Ser Arg Arg Pro Ser Tyr Arg Lys Ile Leu Asn
1               5                   10                  15

Asp Leu Ser Ser Asp Ala Pro
            20

<210> SEQ ID NO 30
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: mod_res
<222> LOCATION: (1)..(1)
<223> OTHER INFORMATION: phosphoserine

<400> SEQUENCE: 30

Ser Tyr Arg Lys Ile Leu Asn Asp Leu Ser Ser Asp Ala Pro
1               5                   10

<210> SEQ ID NO 31
<211> LENGTH: 8
<212> TYPE: PRT
<213> ORGANISM: Artificial Sequence
<220> FEATURE:
<223> OTHER INFORMATION: Synthetic

<400> SEQUENCE: 31

Leu Met Ser Thr Glu Asn Glu Leu
1               5

<210> SEQ ID NO 32

<400> SEQUENCE: 32

000

<210> SEQ ID NO 33
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: mod_res
<222> LOCATION: (1)..(23)
<223> OTHER INFORMATION: D-amino acids
<220> FEATURE:
<221> NAME/KEY: mod_res
<222> LOCATION: (14)..(14)
```

<223> OTHER INFORMATION: phosphoserine

<400> SEQUENCE: 33

Pro Ala Asp Ser Ser Leu Asp Asn Leu Ile Lys Arg Tyr Ser Pro Arg
1               5                   10                  15

Arg Ser Leu Ile Glu Arg Arg
            20

<210> SEQ ID NO 34
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: mod_res
<222> LOCATION: (1)..(14)
<223> OTHER INFORMATION: D-amino acids
<220> FEATURE:
<221> NAME/KEY: mod_res
<222> LOCATION: (14)..(14)
<223> OTHER INFORMATION: phosphoserine

<400> SEQUENCE: 34

Pro Ala Asp Ser Ser Leu Asp Asn Leu Ile Lys Arg Tyr Ser
1               5                   10

<210> SEQ ID NO 35
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: mod_res
<222> LOCATION: (1)..(8)
<223> OTHER INFORMATION: D-amino acids

<400> SEQUENCE: 35

Leu Glu Asn Glu Thr Ser Met Leu
1               5

<210> SEQ ID NO 36
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: mod_red
<222> LOCATION: (1)..(7)
<223> OTHER INFORMATION: D-amino acids
<220> FEATURE:
<221> NAME/KEY: mod_red
<222> LOCATION: (7)..(7)
<223> OTHER INFORMATION: phosphoserine

<400> SEQUENCE: 36

Asn Leu Ile Lys Arg Tyr Ser
1               5

<210> SEQ ID NO 37
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: mod_res
<222> LOCATION: (1)..(1)

```
<223> OTHER INFORMATION: phosphoserine

<400> SEQUENCE: 37

Ser Tyr Arg Lys Ile Leu Asn
1               5

<210> SEQ ID NO 38
<211> LENGTH: 25
<212> TYPE: PRT
<213> ORGANISM: Artificial
<220> FEATURE:
<223> OTHER INFORMATION: Synthetic

<400> SEQUENCE: 38

Tyr Gly Arg Lys Lys Arg Arg Gln Arg Arg Gly Gly Leu Glu Leu Leu
1               5                   10                  15

Leu Met Ser Thr Glu Asn Glu Leu Lys
            20                  25

<210> SEQ ID NO 39
<211> LENGTH: 26
<212> TYPE: PRT
<213> ORGANISM: Artificial
<220> FEATURE:
<223> OTHER INFORMATION: Synthetic
<220> FEATURE:
<221> NAME/KEY: mod_res
<222> LOCATION: (1)..(26)
<223> OTHER INFORMATION: D-amino acids

<400> SEQUENCE: 39

Leu Glu Leu Leu Leu Met Ser Thr Glu Asn Glu Leu Lys Gly Gly Arg
1               5                   10                  15

Arg Arg Gln Arg Arg Lys Lys Arg Gly Tyr
            20                  25
```